(12) United States Patent
Spiegel et al.

(10) Patent No.: US 7,803,595 B2
(45) Date of Patent: *Sep. 28, 2010

(54) MAMMALIAN SPHINGOSINE KINASE TYPE 2 ISOFORMS, CLONING, EXPRESSION AND METHODS OF USE THEREOF

(75) Inventors: Sarah Spiegel, McLean, VA (US); Takafumi Kohama, Tokyo (JP)

(73) Assignees: Sankyo Company, Limited, Tokyo (JP); Georgetown University, Washington, DC (US)

( * ) Notice: Subject to any disclaimer, the term of this patent is extended or adjusted under 35 U.S.C. 154(b) by 370 days.

This patent is subject to a terminal disclaimer.

(21) Appl. No.: 11/891,964

(22) Filed: Aug. 14, 2007

(65) Prior Publication Data

US 2009/0169555 A1    Jul. 2, 2009

Related U.S. Application Data

(62) Division of application No. 10/830,677, filed on Apr. 22, 2004, now Pat. No. 7,419,814, which is a division of application No. 09/817,676, filed on Mar. 26, 2001, now Pat. No. 6,800,470.

(60) Provisional application No. 60/194,318, filed on Apr. 3, 2000.

(51) Int. Cl.
*C12N 9/12* (2006.01)
*C12N 1/20* (2006.01)
*C12Q 1/68* (2006.01)
*C12Q 1/00* (2006.01)
*C12Q 1/48* (2006.01)
*A01N 25/00* (2006.01)
*C07H 21/04* (2006.01)
*C12P 21/04* (2006.01)
*C12N 15/00* (2006.01)

(52) U.S. Cl. .............................. 435/194; 435/4; 435/6; 435/69.1; 435/71.1; 435/252.3; 435/320.1; 435/440; 435/15; 514/789; 536/23.2

(58) Field of Classification Search ....................... None
See application file for complete search history.

(56) References Cited

U.S. PATENT DOCUMENTS 5,374,616 A  12/1994 Spiegel et al.
6,858,427 B2  2/2005 Gerritsen et al.

FOREIGN PATENT DOCUMENTS

WO  WO 98/61581 A  12/1999

OTHER PUBLICATIONS

Spiegel, S., "Sphingosine 1-Phosphate: A Prototype of a New Class of Second Messengers", *J. Leukoc. Biol.*, 65, (1999), 341-344.

Goetzl, E.J., An, S., "Diversity of Cellular Receptors and Functions for the Lysophospholipid Growth Factors Lysophosphatidic Acid and Sphingosine 1-Phosphate", *FASEB J.*, 12, (1998), 1589-1598.

Olivera, A., Spiegel, S., "Sphingosine-1-Phosphate as Second Messenger in Cell Proliferation Induced by PDGF and FCS Mitogens", *Nature*, 365, (1993), 557-560.

Cuvillier, O., Pirianov, G., Kleuser, B., Vanek, P. G., Coso, O. A., Gutkind, S., and Spiegel, S., "Suppression of Ceramide-Mediated Programmed Cell Death by Sphingosine-1-Phosphate", *Nature*, 381, (1996), 800-803).

Pyne, S., Chapman, J. Steele, L., and Pyne, N.J., "Sphigomyelin-Derived Lipids Differentially Regulate the Extracellular Signal-Regulated Kinase 2 (ERK-2) and c-Jun N-Terminal Kinase (JNK) Signal Cascades in Airway Smooth Muscle", *Eur. J. Biochem.*, 237, (1996), 819-826.

Coroneos, E., Martinez, M., McKenna, S. and Kester, M., "Differential Regulation of Sphingomyelinase and Ceramidase Activities by Growth Factors and Cytokines", *J. Biol. Chem.*, 270, (1995), 23305-23309).

Edsall, L. C., Pirianov, G. G., and Spiegel, S., "Involvement of Sphingosine 1-Phosphate in Nerve Growth Factor-Mediated Neuronal Survival and Differentiation", *J. Neurosci.*, 17, (1997), 6952-6960.

Rius, R.A., Edsall, L.C., and Spiegel, S., "Activation of Sphingosine Kinase in Pheochromocytoma PC12 Neuronal Cells in Response to Trophic Factors", *FEBS Lett.*, 417, (1997), 173-176.

Kleuser, B., Cuvillier, O., and Spiegel, S., "$1\alpha$-25-Dihydroxyvitamin $D_3$ Inhibits Programmed Cell Death in HL-60 Cells by Activation of Sphingosine Kinase", *Cancer Res.*, 58, (1998) 1817-1824.

Meyer zu Heringdorf, D., Lass, H., Alemany, R., Laser, K.T., Neumann, E. Zhang: C., Schmidt, M., Rauen, U., Jakobs, K.H., and van Koppen, C.J., "Sphingosine Kinase-Mediated $Ca^{2+}$ Signaling by G-Protein-Coupled Receptors", *EMBO J.*, 17, (1998), 2830-2837.

Xia, P., Gamble, J.R., Rye, K.A., Wang, L., Hii, C.S.T., Cockerill, P., Khew-Goodall, Y., Bert, A.G., Barter, P.J., and Vadas, M.A., "Tumor Necrosis Factor-$\alpha$ Induces Adhesion Molecule Expression Through the Sphingosine Kinase Pathway", *Proc. Natl. Acad. Sci. USA*, 95, (1998), 14196-14201.

Choi, O. H., Kim, J.-H., and Kinet, J.-P., "Calcium Mobilization Via Sphingosine Kinase in Signalling by the Fc$\xi$RI Antigen Receptor", *Nature*, 380, (1996), 634-636.

Melendez, A., Floto, R. A., Gillooly, D. J., Harnett, M. M., and Allen, J.M., "Fc$\gamma$RI Coupling to Phospholipase D Initiates Sphingosine Kinase-Mediated Calcium Mobilization and Vesicular Trafficking", *J. Biol. Chem.*, 273, (1998), 9393-9402.

Mattie, M., Brooker, G, and Spiegel, S., "Sphingosine-1-Phosphate, a Putative Second Messenger, Mobilizes Calcium From Internal Stores Via An Inositol Trisphosphate-Independent Pathway", *J. Biol. Chem.*, 269, (1994), 3181-3188.

Rani, C.S., Berger, A., Wu, J., Sturgill, T. W., Beitner-Johnson, D., LeRoith, D., Varticovski, L., and Spiegel, S., "Divergence in Signal Transduction Pathways of Platelet-Derived Growth Factor (PDGF) and Epidermal Growth Factor (EGF) Receptors", *J. Biol. Chem.*, 272, (1997), 10777-10783.

(Continued)

*Primary Examiner*—Yong D Pak
(74) *Attorney, Agent, or Firm*—Frishauf, Holtz, Goodman & Chick, P.C.

(57) ABSTRACT

Nucleic acids encoding mouse and human sphingosine kinase type 2 isoforms, methods for detecting agents or drugs which inhibit or promote sphingosine activity and therapeutic agents containing peptides or antibodies to peptides encoded by such nucleic acids.

15 Claims, 11 Drawing Sheets

OTHER PUBLICATIONS

Van Brocklyn, J. R., Lee, M. J., Menzeleev, R., Olivera, A., Edsall, L., Cuvillier, O., Thomas, D. M., Coopman, P. J. P., Thangada, S., Hla, T., and Spiegel, S., "Dual Actions of Sphingosine-1-Phosphate: Extracellular Through the $G_1$-Coupled Receptor Edg-1 and Intracellular to Regulate Proliferation and Survival", *J. Cell Biol.*, 142, (1998), 229-240.

Perez, G.I., Knudson, C.M., Leykin, L., Korsmeyer, S.J. and Tilly, J.L., "Apoptsosis-Associated Signaling Pathways Are Required For Chemotherapy-Mediated Female Germ Cell Destruction", *Nature Medicine*, 3, (1997), 1228-1232.

Cuvillier, O., Rosenthal, D. S., Smulson, M. E., and Spiegel, S., "Sphingosine 1-Phosphate Inhibits Activation of Caspases That Cleave Poly (ADP-Ribose) Polymerase and Lamins During Pas- and Ceramide-Mediated Apoptosis in Jurkat T Lymphocytes", *J. Biol. Chem.*, 273, (1998), 2910-2916.

Prieschl, E., E., Csonga, R., Novotny, V., Kikuchi, G. E., and Baumruker, T., "The Balance Between the Sphingosine and Sphingosine-1-Phosphate is Decisive For Mast Cell Activation After Fce Receptor I Triggering", *J. Exp. Med.*, 190, (1999), 1-8.

Lee, M. J., Van Brooklyn, J. R., Thangada, S., Liu, C. H., Hand, A. R., Menzeleev, R., Spiegel, S., and Hla, T., "Sphingosine-1-Phosphate As A Ligand For the G Protein-Coupled Receptor EDG-1", *Science*, 279, (1998), 1552-1555.

Spiegel, S., and Milstein, S., "Functions of a New Family of Sphingosine-1-Phosphate Receptors", *Biochem.Biophys. Acta.*, 1484(2-3):107-116, (2000).

Van Brooklyn, J. R., Tu, Z., Edsall, L. C., Schmidt, R. R., and Spiegel, S., "Sphingosine 1-Phosphate-Induced Cell Rounding and Neurite Retraction Are Mediated by the G Protein-Coupled Receptor H218", *J. Biol. Chem.*, 274, (1999) 4626-4632.

Wang, F., Van Brooklyn, J. R., Hobson, J. P., Movafagh, S., Zukowaka-Grojec, Z., Milstien, S., and Spiegel, S., "Sphingosine 1-Phosphate Stimulates Cell Migration Through a $G_1$-Coupled Cell Surface Receptor", *J. Biol. Chem.*, 274, (1999), 35343-35350.

English, D., Kovala, A. T., Welch, Z., Harvey, K. A., Siddiqui, R. A., Brindley, D. N., and Garcia, J. G., "Induction of Endothelial Cell Chemotaxis by Sphingosine 1-Phosphate and Stabilization of Endothelial Monolayer Barrier Function by Lysophosphatidic Acid, Potential Mediators of Hematopoietic Angiogenesis", *J. Hematother. Stem Cell Res.*, 8, (1999), 627-634.

Lee, O. H., Kim, Y. M., Lee, Y. M., Moon, E. J., Lee, D. J., Kim, J. H., Kim, K. W., and Kwon, Y. G., "Sphingosine 1-Phosphate Induces Angiogenesis: Its Angiogenic Action and Signaling Mechanism in Human Umbilical Vein Endothelial Cells", *Biochem. Biophys. Res. Commun.*, 264, (1999) 743-750.

Lee, M. J., Thangada, S., Claffey, K. P., Ancellini, N., Liu, C. H., Kluk, M., Volpi, Sha'afi, R. I., and Hla, T., "Vascular Endothelial Cell Adherens Junction Assembly and Morphogenesis Induced by Sphingosine-1-Phosphate", *Cell*, 99, (1999), 301-312.

MacLennan, A. J., Marks, L., Gaskin, A. A., and Lee, N., "Embryonic Expression Pattern of H218, A G-Protein Coupled Receptor Homolog, Suggests Roles in Early Mammalian Nervous System Development", *Neuroscience*, 79, (1997), 217-224.

Olivera, A., Kohama, T., Tu, E., Milstien, S., and Spiegel, S., "Purification and Characterization of Rat Kidney Sphingosine Kinase", *J. Biol. Chem.*, 273, (1998), 12576-12583.

Kohama, T., Olivera, A., Edsall, L., Nagiec, M. M., Dickson, R., and Spiegel, S., "Molecular Cloning and Functional Characterization of Murine Sphingosine Kinase", *J. Biol. Chem.*, 273, (1998), 23722-23728.

Nagiec, M. M., Skrzypek, M., Nagiec, E. E., Lester, R. L., and Dickson, R. C., "The LCB4 (YOR171c) and LCB5 (YLR260w) Genes of *Saccharomyces* Encode Sphingoid Long Chain Base Kinases", *J. Biol. Chem.*, 273, (1998) 19437-19442.

Banno, Y., Kato, M., Hara, A., and Nozawa, Y., "Evidence For the Presence of Multiple Forms of Sph Kinase in Human Platelets", *Biochem. J.*, 335, (1998), 301-304.

Olivera, A., Kohama, T., Edsall, L. C., Nava, V., Cuvillier, O., Poulton, S. and Spiegel, S., "Sphingosine Kinase Expression Increases Intracellular Sphingosine-1-Phosphate and Promotes Cell Growth and Survival", *J. Cell Biol.*, 147, (1999), 545-558.

Olivera, A. and Spiegel, S., "Analytical Methods and Steps to Sample Preparation for Determination of Molecular Species of Fatty Acids", *Methods in Molecular Biology*, (Bird, I.M. ed.), (1998), vol. 105, 233-242, Humana Press, Inc., Totowa, H.J.

Edsall, L. C., and Spiegel, S., "Enzymatic Measurement of Sphingosine 1-Phosphate", *Anal. Biochem.*, 272, (1999) 80-86.

Buehrer, B. M., and Bell, R. M., "Inhibition of Sphingosine Kinase In Vitro and In Platelets", *J. Biol. Chem.*, 267, 3154-3159 (1992).

Olivera, A. Rosenthal, J., and Spiegel, S., "Sphingosine Kinase From Swiss 3T3 Fibroblasts: A Convenient Assay For the Measurement of Intracellular Levels of Free Sphingoid Bases", *Anal. Biochem.*, 223, (1994) 306-312.

Ghosh, T. K., Bian, J., and Gill, D. L., "Sphingosine 1-Phosphate Generated In the Endoplasmic Recticulum Membrane Activates Release of Stored Calcium", *J. Biol. Chem.*, 269, (1994), 22628-22635.

Edsall, L. C., Van Brooklyn, J. R., Cuvillier, O., Kleuser, B. and Spiegel, S., "N,N-Dimethylsphingosine Is a Potent Competitive Inhibitor of Sphingosine Kinase but Not of Protein Kinase C: Modulation of Cellular Levels of Sphingosine 1-Phosphate and Ceramide", *Biochemistry*, 37, (1998), 12892-12898.

Machwate, M., Rodan, S. B., Rodan, G. A., and Harada, S. I., "Sphingosine Kinase Mediates Cyclic AMP Suppression of Apoptosis in Rat Periosteal Cells", *Mol. Pharmacol.*, 54, (1998), 70-77.

Olivera, A., Rosenthal, J., and Spiegel, S., "Effect of Acidic Phospholipids on Sphingosine Kinase", *J. Cell. Biochem.*, 60, (1996), 529-537.

Olivera, A., Barlow, K. D., and Spiegel, S., "Assaying Sphingosine Kinase Activity", *Methods Enzymol*, 311, (2000), 215-223.

Johnson, J. E., Zimmerman, M. L., Daleke, D. L., and Newton, A. C., "Light Structure and Not Membrane Structure Is the Major Determinant in the Regulation of Protein Kinase C by Phosphatidylserine", *Biochemistry*, 37, (1998), 12020-12025.

Liu et al., "Molecular Cloning and Functional Characterization of a Novel Mammalian Sphingosine Kinase Type 2 Isoform", *J. Biol. Chem.*, Jun. 2000, vol. 275, No. 26, pp. 19513-19520.

Olivera et al., "Sphingosine Kinase: A Mediator of Vital Cellular Functions", *Prostaglandins & Other Lipid Mediators*, Apr. 2001, vol. 64, No. 1-4, pp. 123-134.

FIG.1A-1

```
                    370              380              390              400              410              420
mSPHK1    ----------RAKSELV LAPAPAAT HSPLHRSV SDLPLPLP QPALYSPG SPEPLP   DLSLNGGGPELTG
mSPHK2    ----------RAKSELT LTPDPAPP MAHSPLHRSV SDLPLPLP QPALYSPG SPEPLP ILSLNGGGPELAG
hSPHK2                                          RPASITLVQKG----- ASPGSPEPLP 430              440              450              460              470              480
mSPHK1    ----------DWGGAGDAPLSPDPLL PSSPNA LKTAQLSPIAEGPP EMPASS I-GFLPPTHSAP EASTWGP
mSPHK2    ----------DWGGAGDAPLSPDPLL SSPPGS PKAALHSPVSEGAP VIPPSSI GLPLPT PDARVGASTCGP 490              500              510              520              530              540
mSPHK1    VDTHLVPLEEPVSHWTVV PEQDFVLVL LHTHLSSELF AAPMGRCEAGVMHLF YIVRAG
mSPHK2    VDHLLPPLGSPLPL PQDWVTL-EGEFVLML GILTSHLCADLMAAPHARF DDGVVHLCWVRSG
hSPHK2    PDHLLPPLGTPLP PDWVTL-EGDFVLML AISPSHLGADLVAAPHARF DDGLVHLCWVRSG 550              560              570              580              590              600
mSPHK1    VSRAALLRL FLAMQKGK HME LDCPYL VHVPVVAF RLEPR SQRGVFISVDGELMVCEAV QGQ
mSPHK2    ISRAALLRI FLAMEHGN HFSLGCPHL GYAAARA FRLEPLT PRGLLTVDGELVEYGPI QAQ
hSPHK2    ISRAALLRL FLAMERGS HFSLGCPQL GYAAARA FRLEPLT PRGVLTVDGEQVEYGPLQAQ
                                                                     C5

610              620              630
mSPHK1    VHPNYLWMVCGSRDAPSGRDSRRG P PEEP
mSPHK2    VHPGLATLLTG------ PAGQK---- PQA
hSPHK2    MHPGIGTLLTG------ PPGCP---- GREP
```

| FIG.1A-1 |
|----------|
| FIG.1A-2 |

MAMMALIAN SPHINGOSINE KINASE TYPE 2 ISOFORMS, CLONING, EXPRESSION AND METHODS OF USE THEREOF

CROSS-REFERENCE TO RELATED APPLICATIONS

This application is a Divisional application of application Ser. No. 10/830,677 filed Apr. 22, 2004 (U.S. Pat. No. 7,419,814), which is a Divisional application of application Ser. No. 09/817,676 filed Mar. 26, 2001 ( U.S. Pat. No. 6,800,470), which claims the benefit under 35 USC 119 (e) of Provisional Application Ser. No. 60/194,318 filed Apr. 3, 2000, said benefit under 35 U.S.C. 119 (e) is also claimed herein.

GOVERNMENT RIGHTS

This invention was made with United States government support under Grant GM 43880 from the National Institutes of Health and a Postdoctoral Fellowship BC961968 from the United States Army Medical Research and Materiel Command, Prostate Cancer Research Program (VEN). The United States government has certain rights in this invention.

BACKGROUND OF THE INVENTION

1. Field of the Invention

The present invention concerns mammalian (such as mouse and human) sphingosine kinase type 2 isoforms, the molecular cloning of such isoforms and methods of use of such isoforms. Sphingosine kinase type 2 has distinct characteristics when compared to sphingosine kinase type 1.

2. Background Information

Sphingosine-1-phosphate (SPP) is a bioactive sphingolipid metabolite which regulates diverse biological processes acting both inside cells as a second messenger to regulate proliferation and survival and outside cells as a ligand for G-protein coupled receptors of the EDG-1 subfamily (Spiegel, S., *J. Leukoc. Biol.*, 65, (1999), 341-344; Goetzl, E. J., An, S. *FASEB J.,* 12, (1998), 1589-1598). Thus, SPP plays important roles as a second messenger to regulate cell growth and survival (Olivera, A., Spiegel, S., *Nature,* 365, (1993), 557-560; Cuvillier, O., Pirianov, G., Kleuser, B., Vanek, P. G., Coso, O. A., Gutkind, S., and Spiegel, S., *Nature,* 381, (1996), 800-803).

Many external stimuli, particularly growth and survival factors, activate sphingosine kinase ("SPHK"), the enzyme that forms SPP from sphingosine. This rapidly growing list includes platelet-derived growth factor ("PDGF") (Olivera, A., Spiegel, S., *Nature,* 365, (1993), 557-560; Pyne, S., Chapman, J. Steele, L., and Pyne, N. J., *Eur. J. Biochem.,* 237, (1996), 819-826; Coroneos, E., Martinez, M., McKenna, S. and Kester, M., *J. Biol. Chem.,* 270, (1995), 23305-23309), nerve growth factor ("NGF") (Edsall, L. C., Pirianov, G. G., and Spiegel, S., *J. Neurosci.,* 17, (1997), 6952-6960; Rius, R. A., Edsall, L. C., and Spiegel, S., *FEBS Lett.,* 417, (1997), 173-176), vitamin D3 (Kleuser, B., Cuvillier, O., and Spiegel, S., *Cancer Res.,* 58, (1998) 1817-1824), muscarinic acetylcholine agonists (Meyer zu Heringdorf, D., Lass, H., Alemany, R., Laser, K. T., Neumann, E. Zhang, C., Schmidt, M., Rauen, U., Jakobs, K. H., and van Koppen, C. J., *EMBO J.,* 17, (1998), 2830-2837), TNF-a (Xia, P., Gamble, J. R., Rye, K. A., Wang, L., Hii, C. S. T., Cockerill, P., Khew-Goodall, Y., Bert, A. G., Barter, P. J., and Vadas, M. A., *Proc. Natl. Acad. Sci. USA,* 95, (1998), 14196-14201), and the cross-linking of the immunoglobulin receptors FceR1 (Choi, O. H., Kim, J.-H., and Kinet, J.-P., *Nature,* 380, (1996), 634-636) and FcgR1 (Melendez, A., Floto, R. A., Gillooly, D. J., Harnett, M. M., and Allen, J. M., *J. Biol. Chem.,* 273 (1998), 9393-9402).

Intracellular SPP, in turn, mobilizes calcium from internal stores independently of InsP3 (Meyer zu Heringdorf, D., Lass, H., Alemany, R., Laser, K. T., Neumann, E. Zhang, C., Schmidt, M., Rauen, U., Jakobs, K. H., and van Koppen, C. J., *EMBO J.,* 17, (1998), 2830-2837; Mattie, M., Brooker, G, and Spiegel, S., *Biol. Chem.,* 269, (1994), 3181-3188), as well as eliciting diverse signaling pathways leading to proliferation (Rani, C. S., Berger, A., Wu, J., Sturgill, T. W., Beitner-Johnson, D., LeRoith, D., Varticovski, L., and Spiegel, S., *J. Biol. Chem.,* 272, (1997), 10777-10783; Van Brocklyn, J. R., Lee, M. J., Menzeleev, R, Olivera, A., Edsall, L., Cuvillier, O., Thomas, D. M., Coopman, P. J. P., Thangada, S., Hla, T., and Spiegel, S., *J. Cell Biol.,* 142, (1998), 229-240) and suppression of apoptosis (Cuvillier, O., Pirianov, G., Kleuser, B., Vanek, P. G., Coso, O. A., Gutkind, S., and Spiegel, S., *Nature,* 381, (1996), 800-803; Edsall, L. C., Pirianov, G. G., and Spiegel, S, *J. Neurosci.,* 17, (1997), 6952-6960; Van Brocklyn, J. R., Lee, M. J., Menzeleev, R., Olivera, A., Edsall, L., Cuvillier, O., Thomas, D. M., Coopman, P. J. P., Thangada, S., Hla, T., and Spiegel S., *J. Cell Biol.,* 142, (1998), 229-240).

Moreover, competitive inhibitors of sphingosine kinase block formation of SPP and selectively inhibit calcium mobilization, cellular proliferation and survival induced by these various stimuli (Spiegel, S., *J. Leukoc. Biol.,* 65, (1999), 341-344). Thus, it has been suggested that the dynamic balance between levels of the sphingolipid metabolites, ceramide and SPP, and the consequent regulation of opposing signaling pathways, is an important factor that determines the fate of cells (Cuvillier, O., Rosenthal, D. S., Smulson, M. E., and Spiegel, S., *J. Biol. Chem.,* 273, (1998), 2910-2916). For example, stress stimuli increase ceramide levels leading to apoptosis, whereas survival factors stimulate SPHK leading to increased SPP levels, which suppress apoptosis (Cuvillier, O., Rosenthal, D. S., Smulson, M. E., and Spiegel, S., *J. Biol. Chem.,* 273, (1998), 2910-2916).

Furthermore, the SPHK pathway, through the generation of SPP, is critically involved in mediating TNF-α-induced endothelial cell activation (Xia, P., Gamble, J. R., Rye, K. A., Wang, L., Hii, C. S. T., Cockerill, P., Khew-Goodall, Y., Bert, A. G., Barter, P. J., and Vadas, M. A., *Proc. Natl. Acad. Sci. USA,* 95, (1998), 14196-14201) and the ability of high density lipoproteins (HDL) to inhibit cytokine-induced adhesion molecule expression has been correlated with its ability to reset this sphingolipid rheostat (Xia, P., Gamble, J. R., Rye, K. A., Wang, L., Hii, C. S. T., Cockerill, P., Khew-Goodall, Y., Bert, A. G., Barter, P. J., and Vadas, M. A., *Proc. Natl. Acad. Sci. USA,* 95, (1998), 14196-14201). This has important implications for the protective function of HDL against the development of atherosclerosis and associated coronary heart disease. Recent data has also connected the sphingolipid rheostat to allergic responses (Prieschl, E., E., Csonga, R., Novotny, V., Kikuchi, G. E., and Baumruker, T., *J. Exp. Med.,* 190, (1999), 1-8).

Interest in SPP has accelerated recently with the discovery that it is a ligand of the G-protein coupled cell surface receptor EDG-1 (Van Brocklyn, J. R., Lee, M. J., Menzeleev, R., Olivera, A., Edsall, L., Cuvillier, O., Thomas, D. M., Coopman, P. J. P., Thangada, S, Hla, T., and Spiegel, S., *J. Cell Biol.,* 142, (1998), 229-240; Lee, M. J., Van Brocklyn, J. R., Thangada, S., Liu, C. H., Hand, A. R., Menzeleev, R., Spiegel, S., and Hla, T., *Science,* 279, (1998), 1552-1555). This rapidly led to the identification of several other related receptors, named EDG-3, -5, -6, and -8, which are also specific SPP receptors (Goetzl, E. J., and An, S., *FASEB J.,* 12, (1998), 1589-1598; Spiegel, S., and Milstein, S., *Biochem. Biophys. Acta.,* 1484(2-3):107-16, (2000)). Sphinganine-1-phosphate, which is structurally similar to SPP and lacks only the trans double bond at the 4-position, but not lysophosphatidic acid or sphingosylphosphorylcholine, also binds to these receptors (Van Brocklyn, J. R., Tu, Z., Edsall, L. C., Schmidt, R. R., and Spiegel, S., *J. Biol. Chem.,* 274, (1999) 4626-4632), demonstrating that EDG-1 belongs to a family of G-protein coupled receptors that bind SPP with high affinity and specificity (Goetzl, E. J. and An, S., *FASEB J.,* 12, (1998), 1589-1598; Spiegel, S. and Milstien, S., *Biochem. Biophys. Acta.,* 1484(2-3):107-116, (2000)).

The EDG-1 family of receptors are differentially expressed, mainly in the cardiovascular and nervous systems, and are coupled to a variety of G-proteins and thus can regulate diverse signal transduction pathways culminating in pleiotropic responses depending on the cell type and relative expression of EDG receptors. Although the biological functions of the EDG-1 family of GPCRs are not completely understood, recent studies suggest that binding of SPP to EDG-1 stimulates migration and chemotaxis (Wang, F., Van Brocklyn, J. R., Hobson, J. P., Movafagh, S., Zukowska-Grojec, Z., Milstien, S., and Spiegel, S. *J. Biol. Chem.,* 274, (1999), 35343-35350; English, D., Kovala, A. T., Welch, Z., Harvey, K. A., Siddiqui, R. A., Brindley, D. N., and Garcia, J. G., *J. Hematother. Stem Cell Res.,* 8, (1999), 627-634), and as a consequence, may regulate angiogenesis (Wang. F., Van Brocklyn, J. R., Hobson, J. P., Movafagh, S., Zukowska-Grojec, Z., Milstien, S., and Spiegel, S. *J. Biol. Chem.,* 274, (1999), 35343-35350; Lee, O. H., Kim, Y. M., Lee, Y. M., Moon, E. J., Lee, D. J., Kim, J. H., Kim, K. W., and Kwon, Y. G., *Biochem. Biophys. Res. Commun.,* 264, (1999) 743-750; Lee, M. J., Thangada, S., Claffey, K. P., Ancellini, N., Liu, C. H., Kluk, M., Volpi, Sha'afi, R. I., and Hla, T., *Cell,* 99, (1999), 301-312). EDG-5 may play a role in cytoskeletal reorganization during neurite retraction, which is important for neuronal differentiation and development (Van Brocklyn, J. R., Tu, Z., Edsall, L. C., Schmidt, R. R., and Spiegel, S., *J. Biol. Chem.,* 274, (1999), 4626-4632; MacLennan, A. J., Marks, L., Gaskin, A. A., and Lee, N., *Neuroscience,* 79, (1997), 217-224).

Critical evaluation of the role of SPP requires cloning of the enzymes that regulate its metabolism. Recently, rat kidney SPHK has been purified to apparent homogeneity (Olivera, A., Kohama, T., Tu, Z., Milstien, S., and Spiegel, S., *J. Biol. Chem.,* 273, (1998), 12576-12583) and subsequently the first mammalian SPHK, designated mSPHK1 (Kohama, T., Olivera, A., Edsall, L., Nagiec, M. M., Dickson, R., and Spiegel, S., *J. Biol. Chem.,* 273, (1998), 23722-23728) was cloned. Independently, two genes, termed LCB4 and LCB5, were also shown to code for SPHKs in *Saccharomyces cerevisiae* (Nagiec, M. M., Skrzypek, M., Nagiec, E. E., Lester, R. L., and Dickson, R. C., *J. Biol. Chem.,* 273, (1998) 19437-19442). Moreover, databases identify homologues of mSPHK1 in numerous widely disparate organisms, including worms, plants and mammals, demonstrating that the enzyme is encoded by a member of a highly conserved gene family (Kohama, T., Olivera, A., Edsall, L., Nagiec, M. M., Dickson, R., and Spiegel, S., *J. Biol. Chem.,* 273, (1998), 23722-23728). Comparison of the predicted amino acid sequences of the known SPHK1s revealed five blocks of highly conserved amino acids (Kohama, T., Olivera, A., Edsall, L., Nagiec, M. M., Dickson, R., and Spiegel, S., *J. Biol. Chem.,* 273, (1998), 23722-23728). However, several lines of evidence indicate that there may be multiple mammalian SPHK isoforms.

The finding that SPHK activity in platelets could be chromatographically fractionated into several forms with differing responses to detergents and inhibition by known SPHK inhibitors, indicate the presence of multiple enzyme forms in human platelets (Banno, Y., Kato, M., Hara, A., and Nozawa, Y., *Biochem. J.,* 335, (1998), 301-304). Moreover, homology searches against a comprehensive nonredundant database revealed that several of the expressed sequence tags (dbEST) at NCBI had significant homology to conserved domains of mSPHK1a (Kohama, T., Olivera, A., Edsall, L., Nagiec, M. M., Dickson, R., and Spiegel, S., *J. Biol. Chem.,* 273, (1998), 23722-23728), yet had substantial sequence differences.

U.S. Pat. No. 5,374,616 concerns compositions containing sphingosylphosphorylcholine for promoting cellular proliferation of mammalian cells.

WO 99/61581 describes DNA fragments which encoded murine sphingosine SPHK1a (381 amino acids) and SPHK1b (388 amino acids).

SUMMARY OF THE INVENTION

It is an object of the present invention to provide isolated and purified DNAs which encode mammalian (such as a mouse or human) sphingosine kinase type 2 isoforms and peptides encoded therefrom.

It is a further object of the present invention to provide recombinant DNA constructs comprising a vector and the above described DNAs and host cells transformed with such recombinant DNA constructs.

It is a still further object of the present invention to furnish a method for producing mouse and human sphingosine type 2 isoform peptides by culturing such host cells.

It is an additional object of the present invention to provide a method for detecting an agent or a drug which inhibits or promotes sphingosine kinase activity.

It is yet another object of the present invention to provide a method for regulating a biological process; for treating or ameliorating a disease resulting from increased or decreased cell proliferation or increased or decreased cell death; and for treating or ameliorating a disease resulting from abnormal migration or motility of cells such as cancer, restenosis or diabetic neuropathy.

The present invention is also directed to an isolated and purified DNA which encodes a peptide of a sphingosine kinase type 2 isoform, the DNA comprising a sequence selected from the group consisting of the sequence of Genbank Accession No. bankit325787 and the sequence of Genbank Accession No. bankit325752.

The present invention also concerns methods for detecting an agent or a drug which inhibits or promotes sphingosine kinase type 2 activity comprising:

(a) providing a recombinant DNA construct as discussed above, into a cell such that sphingosine kinase type 2 isoform is produced in the cell;

(b) adding at least one drug or agent to the cell, and (c) detecting whether or not the drug or agent inhibits or promotes sphingosine kinase type 2 activity by measuring sphingosine kinase-dependent phosphorylation of lipids in the cells and comparing the resultant measurement to a control which did not receive the drug or agent, wherein a decrease in the amount of sphingosine kinase-dependent phosphorylation of lipids as compared to the control indicates an inhibitory drug or agent, or an increase in the amount of sphingosine kinase-dependent phosphorylation of lipids in the cell as compared to the control indicates a stimulatory drug or agent.

As described hereinabove, the present invention also relates to methods of regulating a biological process (such as mitogenesis, apoptosis, neuronal development, chemotaxis, angiogenesis and inflammatory responses) in a mammal comprising administering to a mammal (such as a human) in need thereof, a pharmaceutically effective amount of a peptide as described above.

Also as described hereinabove, the present invention is further directed to methods for the treatment or amelioration of a disease resulting from increased cell death or decreased cell proliferation, comprising administering to a mammal (such as a human) in need thereof, a pharmaceutically effective amount of a peptide as described above.

Further as described above, the present invention also relates to methods for the treatment or administration of a disease resulting from decreased cell death or increased cell proliferation comprising administering to a mammal (such as a human) in need thereof, a pharmaceutically effective amount of an antibody to a peptide as described above.

Additionally as described above, the present invention further concerns methods for treatment or amelioration of a disease resulting from abnormal migration or motility of cells selected from the group consisting of cancer, restenosis and diabetic neuropathy, the method comprising administering to a mammal (such as a human) in need thereof, a pharmaceutically effective amount of an antibody to a peptide as described above.

The present invention further relates to compositions for (a) regulating biological processes, (b) treating or ameliorating diseases resulting from increased cell death or decreased cell proliferation, (c) treating or ameliorating diseases resulting from decreased cell death or increased cell proliferation, or (d) treating or ameliorating diseases resulting from abnormal migration or motility of cells (such. as cancer, restenosis and diabetic neuropathy) comprising (i) a pharmaceutically effective amount of a peptide as described above or an antibody to such peptide as described above, and (ii) a pharmaceutically acceptable carrier.

The present invention also involves a method for screening agents or drugs which reduce or eliminate sphingosine kinase type 2 activity, the method comprising detecting a decrease in sphingosine kinase type 2 enzyme activity in the presence of the agent or drug.

Furthermore, the present invention is directed to a method for detecting the presence of sphingosine kinase type 2 isoform in a sample comprising:

(i) contacting a sample with antibodies which recognize sphingosine kinase type 2; and (ii) detecting the presence or absence of a complex formed between sphingosine kinase type 2 and antibodies specific therefor.

The present invention also concerns a method for detecting sphingosine kinase type 2 in a sample comprising subjecting the sample to a polymerase chain reaction and detecting for the presence of sphingosine kinase type 2.

The present invention is additionally directed to a diagnostic kit for detecting sphingosine kinase type 2 RNA/cDNA in a sample comprising primers or oligonucleotides specific for sphingosine kinase type 2 RNA or cDNA suitable for hybridization to sphingosine kinase type 2 RNA or cDNA and/or amplification of sphingosine kinase type 2 sequences and suitable ancillary reagents.

Sphingosine kinase catalyzes the phosphorylation of sphingosine to yield SPP. Based on sequence homology to murine and human sphingosine kinase-1 (SPHK1), which was recently cloned (Kohama, et al., *J. Biol. Chem.*, 273, 23722-23728, (1998)), the present invention is directed to the cloning, functional characterization, and tissue distribution of a second type of mouse and human sphingosine kinase (mSPHK2 and hSPHK2).

mSPHK2 and hSPHK2 of the present invention encode proteins of 617 and 618 amino acids, respectively, both much larger than SPHK1, and both contain the conserved domains previously found in SPHK1, but their sequences diverge considerably in the centers and at the amino termini. Northern blot analysis of multiple human and murine tissues revealed that SPHK2 mRNA expression was strikingly different from that of SPHK1 and was highest in brain, heart, kidney, testes, and liver. Whereas SPHK1 expression is greatest at mouse embryonic day 7, SPHK2 expression is only detectable at embryonic day 11 and increases thereafter.

Human embryonic 293 kidney cells transiently transfected with mSPHK2 or hSPHK2 expression vectors had marked increases in SPHK activity resulting in elevated SPP levels. Notably, SPHK2 had somewhat different substrate specificity than SPHK1. D-erythro-sphingosine (dihydrosphingosine, DHS) was an even better substrate than D-erythro-sphingosine for SPHK2, while DHS was a potent inhibitor of SPHK1.

SPHK2 also catalyzed the phosphorylation of phytosphingosine and D, L-threo-dihydrosphingosine, albeit to a lesser extent. DMS, a competitive inhibitor of SPHK1, surprisingly was a non-competitive inhibitor of SPHK2. Although increasing ionic strength inhibited SPHK1, KCl and NaCl markedly stimulated SPHK2 activity. Moreover, Triton X-100 and BSA inhibited SPHK2, in contrast to their effects on SPHK1, whereas phosphatidylserine stimulated both types. The data herein indicate that SPHK2 is a novel member of this growing class of lipid kinases, which is important in the regulation of diverse biological processes, including mitogenesis, apoptosis, neuronal development, chemotaxis, angiogenesis, and inflammatory responses.

BRIEF DESCRIPTION OF THE DRAWINGS

For the purposes of illustrating the invention, features, aspects and advantages are shown in the drawings. It is to be understood, however, that the present invention is not limited to that which is depicted in the drawings FIG. 1A shows predicted amino acid sequences of murine and human type 2 sphingosine kinase based on non-ClustalW alignment of the predicted amino acid sequences of ("mSPHK2") (SEQ ID NO: 12) and human sphingosine kinase 2 ("hSPHK2") (SEQ ID NO: 14). Identical and conserved amino acid substitutions are shaded dark and light gray, respectively. The dashes represent gaps in sequences and numbers on the right refer to the amino acid sequence of mSPHK2 (SEQ ID NO: 12). The conserved domains (C1 to C5) are indicated by lines. FIG. 1A also shows the amino acid sequence of mSPHK1 (SEQ ID NO: 15).

Figure 1A-1:
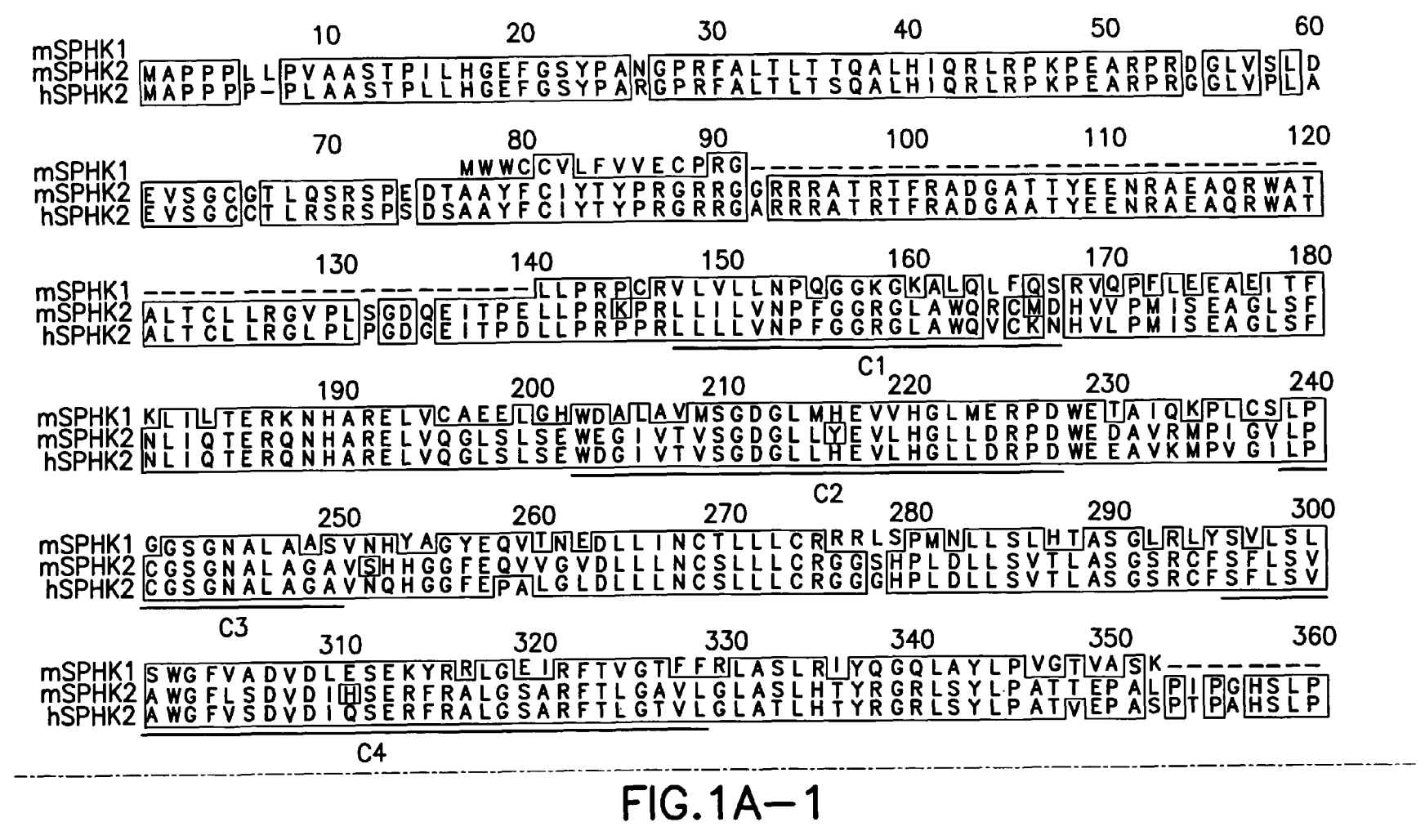

FIG. 1B is a schematic representation of conserved regions of SPHK1 and SPHK2. The primary sequence of mSPHK2 is compared to that of mSPHK1a.

In FIG. 2A, mSPHK2 (upper panel) and mSPHK1a (middle panel) probes were end labeled and hybridized to poly(A)+ RNA blots from the indicated mouse tissues as described hereinbelow. Lanes: 1, heart; 2, brain; 3, spleen; 4, lung; 5, liver; 6, skeletal muscle; 7, kidney; 8, testis. A β-actin probe (lower panel) was used as a loading control.

FIG. 2B shows the tissue specific expression of hSPHK2. Lanes 1, brain; 2, heart; 3, skeletal muscle; 4, colon; 5, thymus; 6, spleen; 7, kidney; 8, liver; 9, small intestine; 10, placenta; 11, lung; 12, leukocyte.

FIG. 2C shows the expression of mSPHK1a and mSPHK2 during mouse embryonic development. Poly(A)+ RNA blots from days 7, 11, 15 and 17 mouse embryos were probed as in FIG. 2A.

In FIG. 3A, HEK 293 cells were transiently transfected with an empty vector or with mSPHK2 or hSPHK2 expression vectors. After 24 hours, SPHK activity was measured in cytosol (open bars) and particulate fractions (filled bars). The data are means±S.D. Parental and vector-transfected cells had basal SPHK activities of 26 and 37 pmol/min/mg, respectively.

FIG. 3B shows the changes in mass levels of SPP after transfection with SPHK2. Mass levels of SPP in HEK293 cells transfected with an empty vector (open bars) or with mSPHK2 (filled bars) or with hSPHK2 (hatched bars) were measured as described hereinbelow. The data are expressed as pmol/nmol phospholipid.

FIG. 4A is a graph which shows SPHK-dependent phosphorylation of various sphingosine analogs or other lipids (50 mM) which was measured in cytosol from HEK293 cells transfected with mSPHK2. Lanes: 1, D-erythro-sphingosine ("D-erythro-Sph"); 2, D-erythro-dihydrosphingosine ("D-erythro-DHS"); 3, D, L-threo-DHS; 4, N,N-dimethylsphingosine ("DMS"); 5, C2-ceramide; 6, C16-ceramide; 7, diacylglycerol; 8, phosphatidylinositol; 9, phytosphingosine. Data are expressed as percentage of phosphorylation of D-erythro-Sph.

FIGS. 4A to 4D are graphs which show the noncompetitive inhibition of recombinant SPHK2 by N,N-dimethylsphingosine.

FIG. 4B shows the dose-dependent inhibition of mSPHK2 by DMS. SPHK activity in HEK293 cell lysates after transfection as in FIG. 4A was measured with 10 µM D-erythro-sphingosine in the presence of increasing concentrations of DMS.

FIG. 4C shows a kinetic analysis of DMS inhibition. SPHK activity was measured with varying concentrations of D-erythro-sphingosine in the absence (open circles) or presence of 10 µM (filled squares) or 20 µM DMS (filled triangles).

FIG. 4D are Lineweaver-Burk plots. The Km for D-erythro-sphingosine was 3.4 µM. The Ki value for DMS was 12 µM.

FIG. 5A shows cytosolic SPHK2 activity in transfected HEK 293 cells that was measured in a kinase buffer with the pH adjusted using the following buffers: 200 mM sodium acetate (pH 4.5-5.5, open circles); 200 mM MES (pH 6-7, filled circles); 200 mM potassium phosphate (pH 6.5-8, open squares); 200 mM HEPES (pH 7-7.5, filled squares); 200 mM Tris-HCl (pH 7.5-9, open triangles); and 200 mM borate (pH 10, filled triangle).

FIGS. 5B to 5E show that salts stimulate SPHK2, but inhibit SPHK1.

In FIGS. 5B and 5C, the SPHK activity in HEK293 cell lysates was measured 24 hours after transfection with mSPHK1 (FIG. 5B) or mSPHK2 (FIG. 5C) in the absence or presence of increasing concentrations of NaCl (open squares) or KCl (filled circles).

FIG. 5D shows a kinetic analysis of SPHK2 activation by KCl. mSPHK2 activity was measured with varying concentrations of D-erythro-sphingosine in the absence (open circles), or presence of 50 mM KCl (open squares), or 200 mM KCl (filled squares).

FIG. 5E are Lineweaver-Burk plots of data from FIG. 5D. The Km value not affected by the presence of KCl. Vmax values were 0.1, 0.3 and 1 (nmol/min/mg) in the presence of 0, 50, and 200 mM KCl, respectively.

DETAILED DESCRIPTION OF THE INVENTION

Figure 1B:
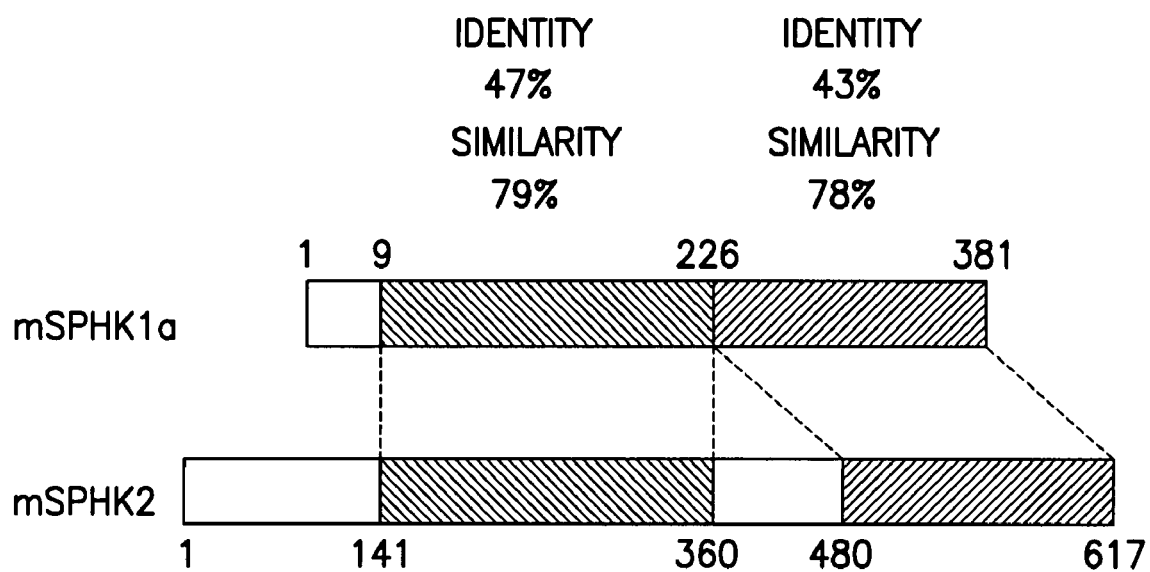

In one embodiment, the present invention relates to a DNA or cDNA segment which encodes mammalian (such as mouse and human) sphingosine kinase type 2 isoforms.

In addition, isolated nucleic acid molecules of the invention include DNA molecules which comprise sequences substantially different from those described above but which, due to the degeneracy of the genetic code, still encode mammalian sphingosine kinase type 2 isoforms. Of course, the genetic code and species-specific codon preferences are well known in the art. Thus, it would be routine for one of ordinary skill in the art to generate the degenerate variants described above, for instance, to optimize codon expression for a particular host (e.g., change codons in the human mRNA to those preferred by a bacterial host such as *E. coli*).

Nucleic acid molecules of the present invention may be in the form of RNA, such as mRNA, or in the form of DNA, including, for instance, cDNA and genomic DNA obtained by cloning or produced synthetically. The DNA may be double-stranded or single-stranded. Single-stranded DNA or RNA may be the coding strand, also known as the "sense strand", or it may be the noncoding strand, also referred to as the "antisense strand".

By "isolated" nucleic acid molecule(s) is intended a nucleic acid molecule, DNA or RNA, which has been removed from its native environment. For example, recombinant DNA molecules contained. in a vector are considered isolated for the purposes of the present invention. Further examples of isolated DNA molecules include recombinant DNA molecules maintained in heterologous host cells or purified (partially or substantially) DNA molecules in solution. Isolated RNA molecules include in vivo or in vitro RNA transcripts of the DNA molecules of the present invention. Isolated nucleic acid molecules according to the present invention further include such molecules produced synthetically.

The present invention is further directed to nucleic acid molecules encoding portions or fragments of the nucleotide sequences described herein. Fragments include portions of the nucleotide sequences of FIG. 1A for mSPHK2 and hSPHK2 at least 10 contiguous nucleotides in length selected from any two integers, one of which representing a 5' nucleotide position and a second of which representing a 3' nucleotide position, where the first nucleotide for each nucleotide sequence in FIG. 1A is position 1. That is, every combination of a 5' and 3' nucleotide position of a fragment at least 10 contiguous nucleotide bases in length or any integer between 10 and the length of an entire nucleotide sequence of mSPHK2 or hSPHK2 of FIG. 1A minus 1.

Further, the present invention includes polynucleotides comprising fragments specified by size, in nucleotides, rather than by nucleotide positions. The present invention includes any fragment size, in contiguous nucleotides, selected from integers between 1 and the entire length of an entire nucleotide sequence minus 1. Preferred sizes include 20 to 50 nucleotides; sizes of 50 to 300 nucleotides are useful as primers and probes. Regions from which typical sequences may be derived include, but are not limited to, for example, regions encoding specific epitopes or domains within said sequence, such as domains C1-C5 shown in FIG. 1A.

In another aspect, the invention provides isolated nucleic acid molecules comprising polynucleotides which hybridize under stringent hybridization conditions to a polynucleotide sequence of the present invention described above, for instance, a nucleic acid sequence shown in FIG. 1A or a specified fragment thereof. By "stringent hybridization conditions" is intended overnight incubation at 42° C. in a solution comprising: 50% formamide, 5×SSC (150 mM NaCl, 15 mM trisodium citrate), 50 mM sodium phosphate (pH 7.6), 5× Denhardt's solution, 10% dextran sulfate, and 20 µg/ml denatured sheared salmon sperm DNA, followed by washing the filters in 0.1×SSC at about 65° C.

The sequences encoding the polypeptides of the present invention or portions thereof may be fused to other sequences which provide additional functions known in the art such as a marker sequence, or a sequence encoding a peptide which facilitates purification of the fused polypeptide, peptides having antigenic determinants known to provide helper T-cell stimulation, peptides encoding sites for post-translational modifications, or amino acid sequences in which target the fusion protein to a desired location, e.g., a heterologous leader sequence.

The present invention further relates to variants of the nucleic acid molecules of the present invention, which encode portions, analogs or derivatives of the sphingosine kinase type 2 isoform polypeptides shown in FIG. 1A. Variants may occur naturally, such as a natural allelic variant. By an "allelic variant" is intended one of several alternate forms of a gene occupying a given locus of a chromosome of an organism. Non-naturally occurring variants may be produced by known mutagenesis techniques. Such variants include those produced by nucleotide substitution, deletion or addition of one or more nucleotides in the coding or noncoding regions or both. Alterations in the coding regions may produce conservative or nonconservative amino acid substitutions, deletions, or additions. Especially preferred among these are silent substitutions, additions, and deletions which do not alter the properties and activities of sphingosine kinase type 2 isoform polypeptides disclosed herein or portions thereof. Also preferred in this regard are conservative substitutions.

Nucleic acid molecules with at least 90-99% identity to a nucleic acid molecule which encodes a sphingosine kinase type 2 isoform shown in FIG. 1A is another aspect of the present invention. These nucleic acids are included irrespective of whether they encode a polypeptide having sphingosine kinase activity. By "a polypeptide having sphingosine kinase type 2 activity" is intended polypeptides exhibiting activity similar, but not identical, to an activity of the sphingosine kinase type 2 isoform of the present invention, as measured in the assays described below. The biological activity or function of the polypeptides of the present invention are expected to be similar or identical to, polypeptides from other organisms that share a high degree of structural identity/similarity.

In another embodiment, the present invention relates to a recombinant DNA molecule that includes a vector and a DNA sequence as described above. The vector can take the form of a plasmid, phage, cosmid, YAC, an eukaryotic expression vector such as a DNA vector, *Pichia pastoris*, or a virus vector such as for example, baculovirus vectors, retroviral vectors or adenoviral vectors, and others known in the art. The cloned gene may optionally be placed under the control of (i.e., operably linked to) certain control sequences such as promoter sequences, or sequences which may be inducible and/or cell type-specific. Suitable promoters are known to a person with ordinary skill in the art. The expression construct will further contain sites for transcription initiation, termination and, in the transcribed region, a ribosome binding site for translation. Among the vectors preferred for use include pCMV-SPORT2 (Life Technologies, Inc.), pcDNA3 (Invitrogen), to name a few.

Introduction of the construct into the host cell can be effected by calcium phosphate transfection, electroporation, infection, and other methods known in the art and described in standard laboratory manuals such as *Current Protocols in Molecular Biology*, Ausubel, F. M. et al. (Eds), Wiley & Sons, Inc. All documents cited herein supra and infra are hereby incorporated in their entirety by reference thereto.

In a further embodiment, the present invention relates to host cells stably transformed or transfected with the above-described recombinant DNA constructs. The host cell can be prokaryotic (for example, bacterial), lower eukaryotic (for example, yeast or insect) or higher eukaryotic (for example, all mammals, including, but not limited to, rat and human).

Both prokaryotic and eukaryotic host cells may be used for expression of desired coding sequences, when appropriate control sequences which are compatible with the designated host are used. Among prokaryotic hosts, *E. coli* is most frequently used. Expression control sequences for prokaryotes include promoters, optionally containing operator portions, and ribosome binding sites. Transfer vectors compatible with prokaryotic hosts are commonly derived from, for example, pBR322, a plasmid containing operons conferring ampicillin and tetracycline resistance, and the various pUC vectors, which also contain sequences conferring antibiotic resistance markers. These markers may be used to obtain successful transformants by selection. See, for example, Maniatis, Fitsch and Sambrook, *Molecular Cloning: A Laboratory Manual*, (1982) or *DNA Cloning*, Volumes I and II (D. N. Glover ed., 1985) for general cloning methods.

A transformant having a plasmid in which a cDNA encoding human SPHK2 is inserted, namely *E. coli* pCR3.1-hSPHK2 SANK 70200 has been deposited with the National Institute of Bioscience and Human-Technology, Agency of Industrial Science and Technology, 1-3, Higashi 1-chome, Tsukuba-shi, Ibaraki-ken 305-8566, Japan, accession number FERM BP-7110, deposited Mar. 29, 2000.

The DNA sequence can be present in the vector operably linked to a sequence encoding an IgG molecule, an adjuvant, a carrier, or an agent for aid in purification of SPHK, such as glutathione S-transferase, or a series of histidine residues also known as a histidine tag. The recombinant molecule can be suitable for transfecting eukaryotic cells, for example, mammalian cells and yeast cells in culture systems. *Saccharomyces cerevisiae*, *Saccharomyces carlsbergensis*, and *Pichia pastoris* are the most commonly used yeast hosts, and are convenient fungal hosts. Control sequences for yeast vectors are known in the art. Mammalian cell lines are available as hosts for expression are known in the art and include many immortalized cell lines available from the American Type Culture Collection (ATCC), such as HEK293 cells, and NIH 3T3 cells, to name a few. Suitable promoters are also known in the art and include viral promoters such as that from SV40, Rous sarcoma virus ("RSV"), adenovirus ("ADV"), bovine papilloma virus ("BPV"), and cytomegalovirus ("CMV").

Mammalian cells may also require terminator sequences and poly A addition sequences; enhancer sequences which increase expression may also be included, and sequences which cause amplification of the gene may also be desirable. These sequences are known in the art.

The transformed or transfected host cells can be used as a source of DNA sequences described above. When the recombinant molecule takes the form of an expression system, the transformed or transfected cells can be used as a source of the protein described below. In another embodiment, the present invention relates to the employment of nucleotide sequences corresponding to GenBank/EMBL Data Bank accession nos. bankit325787 and bankit325752.

A polypeptide or amino acid sequence expressed from the nucleotide sequences discussed above, refers to polypeptide having an amino acid sequence identical to that of a polypeptide encoded from the sequence, or a portion thereof wherein the portion contains at least 2 to 5 amino acids, and more preferably at least 8 to 10 amino acids, and even more preferably at least 15 amino acids, or which is immunologically identifiable with a polypeptide encoded in the sequence.

A recombinant or derived polypeptide is not necessarily translated from a designated nucleic acid sequence; it may be generated in any manner, including, for example, chemical synthesis, or expression of a recombinant expression system. In addition the polypeptide can be fused to other proteins or polypeptides which increase its antigenicity, such as adjuvants, for example.

As noted above, the methods of the present invention are suitable for production of any polypeptide of any length, via insertion of the above-described nucleic acid molecules or vectors into a host cell and expression of the nucleotide sequence encoding the polypeptide of interest by the host cell. Introduction of the nucleic acid molecules or vectors into a host cell to produce a transformed host cell can be effected by calcium phosphate transfection, DEAE-dextran mediated transfection, cationic lipid-mediated transfection, electroporation, transduction, infection or other methods. Such methods are described in many standard laboratory manuals, such as in Davis et al., *Basic Methods In Molecular Biology*, (1986).

Once transformed host cells have been obtained, the cells may be cultivated under any physiologically compatible conditions of pH and temperature, in any suitable nutrient medium containing assimilable sources of carbon, nitrogen and essential minerals that support host cell growth. Recombinant polypeptide-producing cultivation conditions vary according to the type of vector used to transform the host cells. For example, certain expression vectors comprise regulatory regions which require cell growth at certain temperatures, or addition of certain chemicals or inducing agents to the cell growth medium, to initiate the gene expression resulting in the production of the recombinant polypeptide. Thus, the term "recombinant polypeptide-producing conditions," as used herein, is not meant to be limited to any one set of cultivation conditions. Appropriate culture media and conditions for the above-described host cells and vectors are well-known in the art. Following its production in the host cells, the polypeptide of interest may be isolated by several techniques.

To liberate the polypeptide of interest from the host cells, the cells are lysed or ruptured. This lysis may be accomplished by contacting the cells with a hypotonic solution, by treatment with a cell wall-disrupting enzyme such as lysozyme, by sonication, by treatment with high pressure, or by a combination of the above methods. Other methods of bacterial cell disruption and lysis that are known to one of ordinary skill may also be used.

Following disruption, the polypeptide may be separated from the cellular debris by any technique suitable for separation of particles in complex mixtures. The polypeptide may then be purified by well-known isolation techniques. Suitable techniques for purification include, but are not limited to, ammonium sulfate or ethanol precipitation, acid extraction, electrophoresis, immunoadsorption, anion or cation exchange chromatography, phosphocellulose chromatography, hydrophobic interaction chromatography, affinity chromatography, immunoaffinity chromatography, size exclusion chromatography, liquid chromatography (LC), high performance LC (HPLC), fast performance LC (FPLC), hydroxylapatite chromatography and lectin chromatography.

The recombinant or fusion protein can be used as a diagnostic tool and in a method for producing sphingosine-1-phosphate, detectably labeled and unlabeled, and in a method for measuring levels of SPP in samples as described below. In addition, the recombinant protein can be used as a therapeutic agent to reduce cell death and/or increase cell proliferation. The transformed host cells can be used to analyze the effectiveness of drugs and agents which inhibit SPHK2 function, such as host proteins or chemically derived agents or other proteins which may interact with the cell to down-regulate or alter the expression of SPHK2, or its cofactors.

In another embodiment, the present invention relates to monoclonal or polyclonal antibodies specific for the above-described recombinant proteins (or polypeptides). For instance, an antibody can be raised against a peptide described above, or against, a portion thereof of at least 10 amino acids, preferably 11 to 15 amino acids. Persons with ordinary skill in the art using standard methodology can raise monoclonal and polyclonal antibodies to the protein (or polypeptide) of the present invention, or a unique portion thereof. Material and methods for producing antibodies are well known in the art (see, for example, Goding in *Monoclonal Antibodies: Principles and Practice*, Chapter 4, 1986).

The level of expression of sphingosine kinase type 2 can be detected at several levels. Using standard methodology well known in the art, assays for the detection and quantitation of sphingosine kinase type 2 RNA can be designed and include northern hybridization assays, in situ hybridization assays, and PCR assays, among others. See, for example, Maniatis, Fitsch and Sambrook, *Molecular Cloning, A Laboratory Manual*, (1982) or *DNA Cloning*, Volumes I and II (D. N. Glover ed. 1985), or *Current Protocols in Molecular Biology*, Ausubel, F. M. et al., (Eds), Wiley & Sons, Inc. for a general description of methods for nucleic acid hybridization.

Polynucleotide probes for the detection of sphingosine kinase type 2 RNA can be designed from the sequence available at accession numbers AF068748 and/or AF068749 for the mouse sequence (Kohama, T., et al., *J. Biol. Chem.*, 273: 23722-23728). For example, RNA isolated from samples can be coated onto a surface such as a nitrocellulose membrane and prepared for northern hybridization. In the case of in situ hybridization of biopsy samples, for example, the tissue sample can be prepared for hybridization by standard methods known in the art and hybridized with polynucleotide sequences which specifically recognize sphingosine kinase type 2 RNA. The presence of a hybrid formed between the sample RNA and the polynucleotide can be detected by any method known in the art such as radiochemistry, or immunochemistry, to name a few.

One of skill in the art may find it desirable to prepare probes that are fairly long and/or encompass regions of the amino acid sequence which would have a high degree of redundancy in the corresponding nucleic acid sequences. In other cases, it may be desirable to use two sets of probes simultaneously, each to a different region of the gene. While the exact length of any probe employed is not critical, typical probe sequences are no greater than 500 nucleotides, even more typically they are no greater than 250 nucleotides; they may be no greater than 100 nucleotides, and also may be no greater than 75 nucleotides in length. Longer probe sequences may be necessary to encompass unique polynucleotide regions with differences sufficient to allow related target sequences to be distinguished. For this reason, probes are preferably from about 10 to about 100 nucleotides in length and more preferably from about 20 to about 50 nucleotides.

The DNA sequence of sphingosine kinase type 2 can be used to design primers for use in the detection of sphingosine kinase type 2 using the polymerase chain reaction (PCR) or reverse transcription PCR (RT-PCR). The primers can specifically bind to the sphingosine kinase type 2 cDNA produced by reverse transcription of sphingosine kinase type 2 RNA, for the purpose of detecting the presence, absence, or quantifying the amount of sphingosine kinase type. 2 by comparison to a standard. The primers can be any length ranging from 7 to 40 nucleotides, preferably 10 to 35 nucleotides, most preferably 18 to 25 nucleotides homologous or complementary to a region of the sphingosine kinase type 2 sequence.

Reagents and controls necessary for PCR or RT-PCR reactions are well-known in the art. The amplified products can then be analyzed for the presence or absence of sphingosine kinase type 2 sequences, for example, by gel fractionation, by radiochemistry, and immunochemical techniques. This method is advantageous, since it requires a small number of cells. Once sphingosine kinase type 2 is detected, a determination of whether the cell is overexpressing or underexpressing sphingosine kinase type 2 can be made by comparison to the results obtained from a normal cell using the same method. Increased sphingosine kinase type 2 RNA levels correlate with increased cell proliferation and reduced cell death.

In another embodiment, the present invention relates to a diagnostic kit for the detection of sphingosine kinase type 2 RNA in cells. The kit comprises a package unit having one or more containers of sphingosine kinase type 2 oligonucleotide primers for detection of sphingosine kinase type 2 by PCR or RT-PCR or sphingosine kinase type 2 polynucleotides for the detection of sphingosine kinase type 2 RNA in cells by in situ hybridization or Northern analysis and, in some kits, including containers of various reagents used for the method desired. The kit may also contain one or more of the following items: polymerization enzymes, buffers, instructions, controls and detection labels. Kits may include containers of reagents mixed together in suitable proportions for performing the methods in accordance with the invention. Reagent containers preferably contain reagents in unit quantities that obviate measuring steps when performing the subject methods.

In a further embodiment, the present invention provides a method for identifying and quantifying the level of sphingosine kinase type 2 present in a particular biological sample. Any of a variety of methods which are capable of identifying (or quantifying) the level of sphingosine kinase type 2 in a sample can be used for this purpose.

Diagnostic assays to detect sphingosine kinase type 2 may comprise biopsy or in situ assay of cells from an organ or tissue sections, as well as an aspirate of cells from a tumor or normal tissue. In addition, assays may be conducted upon cellular extracts from organs, tissues, cells, urine, or serum or blood or any other body fluid or extract.

When assaying a biopsy, the assay will comprise contacting the sample to be assayed with a sphingosine kinase type 2 ligand, natural or synthetic, or an antibody, polyclonal or monoclonal, which recognizes sphingosine kinase type 2, or an antiserum capable of detecting sphingosine kinase type 2, and detecting the complex formed between sphingosine kinase type 2 present in the sample and the sphingosine kinase type 2 ligand or antibody added.

Sphingosine kinase type 2 ligands or substrates include for example, sphingosine, in addition to natural and synthetic classes of ligands and their derivatives which can be derived from natural sources such as animal or plant extracts. Other sphingosine kinase type 2 ligands include calmodulin.

Sphingosine kinase type 2 ligands or anti-sphingosine kinase type 2 antibodies, or fragments of ligand and antibodies capable of detecting sphingosine kinase type 2 may be labeled using any of a variety of labels and methods of labeling for use in diagnosis and prognosis of disease associated with increased cell proliferation, such as cancer, or reduced cell death. Examples of types of labels which can be used in the present invention include, but are not limited to enzyme labels, radioisotopic labels, nonradioactive isotopic labels, and chemiluminescent labels.

Examples of suitable enzyme labels include malate dehydrogenase, staphylococcal nuclease, delta-5-steroid isomerase, yeast-alcohol dehydrogenase, alpha-glycerol phosphate dehydrogenase, triose phosphate isomerase, peroxidase, alkaline phosphatase, asparaginase, glucose oxidase, beta-galactosidase, ribonuclease, urease, catalase, glucose-6-phosphate hydrogenase, glucoamylase, acetylcholine esterase, etc.

Examples of suitable radioisotopic labels include $^3$H, $^{111}$In, $^{125}$I, $^{32}$P, $^{35}$S, $^{14}$C, $^{57}$To, $^{58}$Co, $^{59}$Fe, $^{75}$Se, $^{152}$Eu, $^{90}$Y, $^{67}$Cu, $^{21}$Ci, $^{211}$At, $^{212}$Pb, $^{47}$Sc, $^{109}$Pd, $^{11}$C, $^{19}$F and $^{131}$I.

Examples of suitable non-radioactive isotopic labels include $^{157}$Gd, $^{55}$Mn, $^{162}$Dy, $^{52}$Tr and $^{46}$Fe.

Examples of suitable fluorescent labels include a $^{152}$Eu label, a fluorescein label, an isothiocyanate I label, a rhodamine label, a phycoerythrin label, a phycocyanin label, an allophycocyanin label and a fluorescamine label.

Examples of chemiluminescent labels include a luminal label, an isoluminal label, an aromatic acridinium ester label, an imidazole label, an acridinium salt label, an oxalate ester label, a luciferin label and a luciferase label.

Those of ordinary skill in the art will know of other suitable labels which may be employed in accordance with the present invention. The binding of these labels to ligands and to antibodies or fragments thereof can be accomplished using standard techniques commonly known to those of ordinary skill in the art. Typical techniques are described by Kennedy, J. H., et al., (1976), *Clin. Chem. Acta.*, 70, 1-31, and Schurs, A. H. W. M., et al., (1977), *Clin. Chem. Acta.*, 81, 1-40. Coupling techniques mentioned in the latter are the glutaraldehyde method, the periodate method, the dalemide method, and others.

The detection of the antibodies (or fragments of antibodies) of the present invention can be improved by the use of carriers. Well-known carriers include glass, polystyrene, polypropylene, polyethylene, dextran, nylon, amylases, natural and modified celluloses, polyacrylamides, agaroses, and magnetite. The nature of the carrier can be either soluble to some extent or insoluble for the purposes of the present invention. The support material may have virtually any possible structural configuration, so long as the coupled molecule is capable of binding to sphingosine kinase type 2. Thus, the support configuration may be spherical, as in a bead, or cylindrical, as in the inside surface of a test tube, or the external surface of a rod. Alternatively, the surface may be flat such as a sheet or test strip. Those of ordinary skill in the art will know many other suitable carriers for binding monoclonal antibody, or will be able to ascertain the same by the use of routine experimentation.

The ligands or antibodies, or fragments of antibodies or ligands of sphingosine kinase type 2 discussed above may be used to quantitatively or qualitatively detect the presence of sphingosine kinase type 2. Such detection may be accomplished using any of a variety of immunoassays known to persons of ordinary skill in the art such as radioimmunoassays, immunometric assays, etc. Using standard methodology well known in the art, a diagnostic assay can be constructed by coating on a surface (i.e., a solid support) for example, a microtitration plate or a membrane (e.g., a nitrocellulose membrane), antibodies specific for sphingosine kinase type 2 or a portion of sphingosine kinase type 2, and contacting it with a sample from a person suspected of having a sphingosine kinase type 2 related disease. The presence of a resulting complex formed between sphingosine kinase type 2 in the sample and antibodies specific therefor can be detected by any of the known detection methods common in the art, such as fluorescent antibody spectroscopy or colorimetry. A good description of a radioimmune assay may be found in *Laboratory Techniques and Biochemistry* in *Molecular Biology* by Work, T. S., et al., North Holland Publishing Company, N.Y. (1978), incorporated by reference herein. Sandwich assays are described by Wide at pages 199-206 of *Radioimmune Assay Method*, edited by Kirkham and Hunter, E. & S. Livingstone, Edinburgh, 1970.

The diagnostic methods of this invention are predictive of proliferation and metastatic potentials in patients suffering from cancers including carcinomas of the lung, such as small cell carcinoma, large cell carcinoma, squamous carcinoma, and adenocarcinoma, stomach carcinoma, prostatic adenocarcinoma, ovarian carcinoma such as serous cystadenocarcinoma and mucinous cystadenocarcinoma, ovarian germ cell tumors, testicular carcinomas, and germ cell tumors, pancreatic adenocarcinoma, biliary adenocarcinoma, heptacellular carcinoma, renal cell adenocarcinoma, endometrial carcinoma including adenocarcinomas and mixed Mullerian tumors (carcinosarcomas), carcinomas of the endocervix, ectocervix, and vagina such as adenocarcinoma and squamous carcinoma, basal cell carcinoma, melanoma, and skin appendage tumors, esophageal carcinoma, carcinomas of the nasopharynx and oropharynx including squamous carcinoma and adenocarcinomas, salivary gland carcinomas, brain and central nervous system tumors, including tumors of glial, neuronal, and meningeal origin, tumors of peripheral nerve, soft tissue sarcomas and sarcomas of bone and cartilage. Cells of these tumors which express increased levels of sphingosine kinase type 2, RNA or sphingosine kinase type 2 protein, have increased proliferation and decreased cell death.

The protein can be used to identify inhibitors of sphingosine kinase type 2 activity. Using an enzyme assay, natural and synthetic agents and drugs can be discovered which result in a reduction or elimination of sphingosine kinase type 2 enzymatic activity. Knowledge of the mechanism of action of the inhibitor is not necessary as long as a decrease in the activity of sphingosine kinase type 2 is detected. Inhibitors may include agents or drugs which either bind or sequester the enzyme's substrate(s) or cofactor(s), or inhibit the enzyme itself directly, for example, by irreversible binding of the agent or drug to the enzyme or indirectly, for example, by introducing an agent which binds the sphingosine kinase type 2 substrate. Agents or drugs related to the present invention may result in partial or complete inhibition of sphingosine kinase type 2 activity.

Inhibitors of sphingosine kinase type 2 include DL-threo-dihydrosphingosine (DHS) and the more recently discovered inhibitor N,N-dimethylsphingosine ("DMS") described in Edsall, L. C. et al., (1998), *Biochemistry*, 37, 12892-12898. Inhibitors of sphingosine kinase type 2 may be used in the treatment or amelioration of diseases such as cancer, atherosclerosis, neurodegenerative disorders, i.e., stroke and Alzheimer's disease.

Agents which decrease the level of sphingosine kinase type 2 (i.e., in a human or an animal) or reduce or inhibit sphingosine kinase type 2 activity may be used in the therapy of any disease associated with the elevated levels of sphingosine kinase type 2 or diseases associated with increased cell proliferation, such as cancer. An increase in the level of sphingosine kinase type 2 is determined when the level of sphingosine kinase type 2 in a tumor cell is about 2 to 3 times the level of sphingosine kinase type 2 in the normal cell, up to about 10 to 100 times the amount of sphingosine kinase type 2 in a normal cell. Agents which decrease sphingosine kinase type 2 RNA include, but are not limited to, one or more ribozymes capable of digesting sphingosine kinase type 2 RNA, or antisense oligonucleotides capable of hybridizing to sphingosine kinase type 2 RNA, such that the translation of sphingosine kinase type 2 is inhibited or reduced resulting in a decrease in the level of sphingosine kinase type 2. These antisense oligonucleotides can be administered as DNA, as DNA entrapped in proteoliposomes containing viral envelope receptor proteins (Kanoda, Y. et al., (1989), *Science*, 5, 243, 375) or as part of a vector which can be expressed in the target cell such that the antisense DNA or RNA is made. Vectors which are expressed in particular cell types are known in the art, for example, for the mammary gland. See Furth, *J. Mammary Gland Biol. Neopl.*, 2, (1997), 373, for examples of conditional control of gene expression in the mammary gland.

Alternatively, the DNA can be injected along with a carrier. A carrier can be a protein such as a cytokine, for example, interleukin or a polylysine-glycoprotein carrier. Such carrier proteins and vectors and methods of using same are known in the art. In addition, the DNA could be coated onto tiny gold beads and such beads can be introduced into the skin with, for example, a gene gun (Ulmer, T. B. et al., *Science*, 259, (1993), 1745).

Alternatively, antibodies, or compounds capable of reducing or inhibiting sphingosine kinase type 2, that is reducing or inhibiting either the expression, production or activity of sphingosine kinase type 2, such as antagonists, can be provided as an isolated and substantially purified protein, or as part of an expression vector capable of being expressed in the target cell, such that the sphingosine kinase type 2 reducing or inhibiting agent is produced. In addition, co-factors such as various ions, i.e., $Ca^{2+}$ or factors which affect the stability of the enzyme can be administered to modulate the expression and function of sphingosine kinase type 2. These formulations can be administered by standard routes. In general, the combinations may be administered by the topical, transdermal, intraperitoneal, oral, rectal, or parenteral (e.g., intravenous, subcutaneous, or intramuscular) route. In addition, sphingosine kinase type 2 inhibiting compounds may be incorporated into biodegradable polymers being implanted in the vicinity of where drug delivery is desired, for example, at the site of a tumor so that the sphingosine kinase type 2 inhibiting compound is slowly released systemically. The biodegradable polymers and their use are described, for example, in detail in Brem et al., *J. Neurosurg.*, 74, (1991), 441-446. These compounds are intended to be provided to recipient subjects in an amount sufficient to effect the inhibition of sphingosine kinase type 2. Similarly, agents which are capable of negatively affecting the expression, production, stability or function of sphingosine kinase type 2, are intended to be provided to recipient subjects in an amount sufficient to effect the inhibition of sphingosine kinase type 2. An amount is said to be sufficient to "effect" the inhibition or induction of sphingosine kinase type 2 if the dosage, route of administration, etc., of the agent are sufficient to influence such a response.

In line with the function of sphingosine kinase type 2 in cell proliferation, agents which stimulate the level of sphingosine kinase type 2, such as agonists of SPHK2, may be used in the therapy of any disease associated with a decrease of SPHK2, or a decrease in cell proliferation, wherein SPHK2 is capable of increasing such proliferation, e.g., developmental retardation.

In providing a patient with agents which modulate the expression or function of sphingosine kinase type 2 to a recipient patient, the dosage of administered agent will vary depending upon such factors as the patient's age, weight, height, sex, general medical condition, previous medical history, etc. In general, it is desirable to provide the recipient with a dosage of agent which is in the range of from about 1 pg/kg to 10 mg/kg (body weight of patient), although a lower or higher dosage may be administered.

A composition is said to be "pharmacologically acceptable" if its administration can be tolerated by a recipient patient. Such an agent is said to be administered in a "therapeutically effective amount", if the amount administered is physiologically significant. An agent is physiologically significant if its presence results in a detectable change in the physiology of a recipient patient. The compounds of the present invention can be formulated according to known methods to prepare pharmaceutically useful compositions, whereby these materials, or their functional derivatives, are combined in admixture with a pharmaceutically acceptable carrier vehicle. Suitable vehicles and their formulation, inclusive of other human proteins, e.g., human serum albumin, are described, for example, in *Remington's Pharmaceutical Sciences*, 16th Ed., Osol, A. ed., Mack Easton, Pa. (1980). In order to form a pharmaceutically acceptable composition suitable for effective administration, such compositions will contain an effective amount of the above-described compounds together with a suitable amount of carrier vehicle.

Additional pharmaceutical methods may be employed. to control the duration of action. Control release preparations may be achieved through the use of polymers to complex or absorb the compounds. The controlled delivery may be exercised by selecting appropriate macromolecules (for example, polyesters, polyamino acids, polyvinyl, pyrrolidone, ethylenevinylacetate, methylcellulose, carboxymethylcellulose, or protamine sulfate) and the concentration of macromolecules as well as the method of incorporation in order to control release. Another possible method to control the duration of action by controlled release preparations is to incorporate the compounds of the present invention into particles of a polymeric material, such as polyesters, polyamino acids, hydrogels, poly(lactic acid) or ethylene vinylacetate copolymers. Alternatively, instead of incorporating these agents into polymeric particles, it is possible to entrap these materials in microcapsules prepared, for example, interfacial polymerization, for example, hydroxymethylcellulose for gelatin-microcapsules and poly(methylmethacrylate)-microcapsules, respectively, or in colloidal drug delivery systems, for example, liposomes, albumin microspheres, microemulsions, nanoparticles, and nanocapsules or in macroemulsions. Such techniques are disclosed in *Remington's Pharmaceutical Sciences* (1980).

The present invention also provides kits for use in the diagnostic or therapeutic methods described above. Kits according to this aspect of the invention may comprise one or more containers, such as vials, tubes, ampules, bottles and the like, which may comprise one or more of the compositions of the invention.

The kits of the present invention may comprise one or more compounds or compositions of the present invention, and one or more excipients, diluents or adjuvants.

Having now described the present invention in detail, the same will be more clearly understood by reference to the following examples, which are included herewith for purposes of illustration only and are not intended to be limiting of the present invention.

The following Materials and Methods were used in the Examples described below.

EXAMPLES

Materials

SPP, sphingosine, and N,N-dimethylsphingosine were from Biomol Research Laboratory Inc. (Plymouth Meeting, Pa.). All other lipids were purchased from Avanti Polar Lipids (Birmingham, Ala.). [g-32P]ATP (3000 Ci/mmol) was purchased from Amersham (Arlington Heights, Ill.). Poly-L-lysine and collagen were obtained from Boehringer Mannheim (Indianapolis, Ind.). Restriction enzymes were obtained from New England Biolabs (Beverly, Mass.). Poly (A)+ RNA blots of multiple mouse adult tissues were purchased from Clontech (Palo Alto, Calif.). "Lipofectamine PLUS" and "Lipofectamine" were obtained from Life Technologies, Inc. (Gaithersburg, Md.).

Example 1 cDNA Cloning of Murine Sphingosine Kinase Type 2 (mSPHK2)

BLAST searches of the EST database identified a mouse EST clone (GenBank® accession number AA839233) which had significant homology to conserved domains of mSPHK1a (Kohama, T., Olivera, A., Edsall, L., Nagiec, M. M., Dickson, R. and Spiegel, S., *J. Biol. Chem.*, 273, (1998), 23721-23728), yet had substantial sequence differences. Using this EST, a second isoform of SPHK, denoted mSPHK2, was cloned by two different PCR approaches.

In the first approach, the method PCR cloning from a mouse cDNA library (Stratagene, La Jolla, Calif.) was used. Approximately $1\times10^6$ phage were plated on twenty 150 mm plates, plaques were collected, and plasmids were isolated using standard procedures (Ausubel, F. M., Brent, R., Kingston, R. E., Moore, D. D., Smith, J. A., Seidman, J. G., and Struhl, K., *Current Protocols in Molecular Biology*, Green Publishing Associates and Wiley-Interscience, New York (1987)). An initial PCR reaction was carried out with a sequence specific primer (M-3-1, 5'-CCTGGGTGCACCT-GCGCCTGTATTGG (SEQ ID NO: 1)) and the M13 reverse primer. The longest PCR products were gel purified and used as the template for a second PCR which contained a sequence specific antisense primer (M-3-2, 5'-CCAGTCT-TGGGGCAGTGGAGAGCC-3' (SEQ ID NO:2)) and the T3 primer. The final PCR products were subcloned using a "TOPO TA" cloning kit (Invitrogen) and then sequenced. Platinum high fidelity DNA polymerase (Life Technologies) was used for the PCR amplifications with the following cycling parameters: 30 cycles of 94° C. for 30 seconds, 55° C. for 45 seconds, and 70° C. for 2 minutes with a final primer extension at 72° C. for 5 minutes.

In a second approach, 5'RACE PCR was performed with the 5'RACE System for Rapid Amplification of cDNA ends according to the manufacturer's protocol (Life Technologies). Poly(A)+ RNA was isolated from Swiss 3T3 fibroblasts using a Quick Prep mRNA Purification kit (Pharmacia). The first strand cDNA was synthesized at 42° C. for 50 minutes with 5 mg of Swiss 3T3 poly(A)+ RNA using a target antisense primer designed from the sequence of AA839233 (m-GSP1, 5'-AGGTAGAGGCTTCTGG (SEQ ID NO:3)) and SuperScript II reverse transcriptase (Life Technologies). Two consecutive PCR reactions using this cDNA as a template and LA Taq polymerase (TaKaRa) were carried out as follows: first PCR, 94° C. for 2 minutes followed by 30 cycles of 94° C. for 1 minute, 55° C. for 1 minute, 72° C. for 2 minutes, and primer extension at 72° C. for 5 minutes with 5'RACE Abridged Anchor Primer, 5'-GGCCACGCGTC-GACTAGTACGGGIIGGGIIGGGIIG (SEQ ID NO:4) and the target specific antisense primer m-GSP2, 5'-GC-GATGGGTGAAAGCTGAGCTG (SEQ ID NO:5); for the second PCR, the same conditions were employed, except that the annealing temperature was 65° C., with Abridged Universal Amplification Primer (AUAP), 5'-GGCCACGCGTC-GACTAGTAC (SEQ ID NO:6) and m-GSP3, 5'-AGTCTC-CAGTCAGCTCTGGACC (SEQ ID NO:7). PCR products were cloned into pCR2.1 and sequenced. The PCR products were subcloned into pCR3.1 and pcDNA 3 expression vectors.

Example 2 cDNA Cloning of Human Sphingosine Kinase-2(hSPHK2)

Poly(A)+ RNA from HEK293 cells was used for a 5'RACE reaction. Target specific antisense primers (h-GSP1, 5'-CCCACTCACTCAGGCT (SEQ ID NO:8); h-GSP2, 5'-GAAGGACAGCCCAGCTTCAGAG (SEQ ID NO:9); and h-GSP3, 5'-ATTGACCAATAGAAGCAACC (SEQ ID NO:10)) were designed according to the sequence of a human EST clone (accession number AA295570). A first strand cDNA was synthesized with 5 µg of HEK293 mRNA and h-GSP1. This cDNA was used as a template in an initial PCR reaction using 5'RACE Abridged Anchor Primer and h-GSP2. Then, a nested PCR was carried out using the AUAP primer and h-GSP3. The resulting PCR products were cloned and sequenced as described above.

Example 3

Overexpression and Activity of SPHK2

Human embryonic kidney cells (HEK293, ATCC CRL-1573) and NIH 3T3 fibroblasts (ATCC CRL-1658) were cultured as described in Olivera, A., Kohama, T., Edsall, L. C., Nava, V., Cuvillier, O., Poulton, S., and Spiegel, S., *J. Cell Biol.*, 147, (1999), 545-558. HEK293 cells were seeded at $6 \times 10^5$ per well in poly-L-lysine coated 6 well plates. After 24 hours, cells were transfected with 1 µg of vector alone or with vectors containing sphingosine kinase constructs and 6 µl of "Lipofectamine PLUS" reagent plus 4 µl of "Lipofectamine" reagent per well. One to three days after transfection, cells were harvested and lysed by freeze-thawing as described in Kohama, T., Olivera, A., Edsall, L., Nagiec, M. M., Dickson, R., and Spiegel, S., *J. Biol. Chem.*, 273, (1998), 23722-23728. In some experiments, cell lysates were fractionated into cytosol and membrane fractions by centrifugation at 100,000×g for 60 minutes. SPHK activity was determined in the presence of sphingosine, prepared as a complex with 4 mg/ml BSA, and [g-32P]ATP in kinase buffer (Olivera, A. and Spiegel, S. in *Methods in Molecular Biology*, (Bird, I. M. ed.), (1998), Vol. 105, 233-242, Humana Press, Inc., Totowa, N.J.), containing 200 mM KCl, unless indicated otherwise. 32P-SPP was separated by TLC and quantified with a phosphoimager as previously described.

Example 4

Lipid Extraction and Measurement of SPP

Cells were washed with PBS and scraped in 1 ml of methanol containing 2.5 µl concentrated HCl. Lipids were extracted by adding 2 ml chloroform/1M NaCl (1:1, v/v) and 100 µl 3N NaOH and phases separated. The basic aqueous phase containing SPP, and devoid of sphingosine, ceramide, and the majority of phospholipids, was transferred to a siliconized glass tube. The organic phase was re-extracted with 1 ml methanol/1M NaCl (1:1, v/v) plus 50 µl 3N NaOH, and the aqueous fractions were combined. Mass measurement on SPP in the aqueous phase and total phospholipids in the organic phase were measured exactly as described in Edsall, L. C., Pirianov, G. G., and Spiegel, S., *J. Neurosci.*, 17, (1997) 6952-6960; Edsall, L. C., and Spiegel, S., *Anal. Biochem.*, 272, (1999) 80-86).

Example 5

Northern Blotting Analysis

Poly(A)+ RNA blots containing 2 µg of poly(A)+ RNA per lane from multiple adult mouse and human tissues and mouse embryos were purchased from Clontech. Blots were hybridized with the 1.2 kb PSTI fragment of mouse EST AA389187 (mSPHK1 probe), the 1.5 kb EcoRI fragment of pCR3.1-mSPHK2, or the 0.3 kb PvuII fragment of pCR3.1-hSPHK1, after gel-purification and labeling with [a-32P]dCTP. Hybridization in "ExpressHyb" buffer (Clontech) at 65° C. overnight was carried out according to the manufacturer's protocol. Blots were reprobed with b-actin as a loading control (Clontech). Bands were quantified using a Molecular Dynamics Phosphoimager.

Results

Cloning of Type 2 Sphingosine Kinase

Blast searches of the EST data base identified several ESTs that displayed significant homology to the recently cloned mSPHK1a sequence. Specific primers were designed from the sequences of these ESTs and were used to clone a new type of mouse and human sphingosine kinase (named mSPHK2 and hSPHK2) by the approaches of PCR cloning from a mouse brain cDNA library and 5'-RACE PCR.

ClustalW alignment of the amino acid sequences of mSPHK2 and hSPHK2 is shown in FIG. 1A. The open reading frames of mSPHK2 and hSPHK2 encode polypeptides of 617 and 618 amino acids, respectively, with 83% identity and 90% similarity. Five highly conserved regions (C1 to C5), identified previously in SPHK1s (Kohama, T., Olivera, A., Edsall, L., Nagiec, M. M., Dickson, R., Spiegel, S., *J. Biol. Chem.*, 273, (1998) 23722-23728), are also present in both type 2 kinases. Interestingly, the invariant GGKGK positively charged motif in the C1 domain of SPHK1 is modified to GGRGL in SPHK2, suggesting that it may not be part of the ATP binding site as previously proposed (Kohama, T., Olivera, A., Edsall, L., Nagiec, M. M., Dickson, R., Spiegel, S., *J. Biol. Chem.*, 273, (1998) 23722-23728). A motif search also revealed that a region beginning just before the conserved C1 domains of mSPHK2 and hSPHK2 (amino acid 147 to 284) also has homology to the diacylglycerol kinase catalytic site.

Compared to SPHK1, both SPHK2s encode much larger proteins containing 236 additional amino acids (FIG. 1B). Moreover, their sequences diverge considerably from SPHK1 in the center and at the amino termini. However, after amino acid 140 of mSPHK2, the sequences of type 1 and type 2 SPHK have a large degree of similarity. These sequences (amino acid 9 to 226 for mSPHK1; 141 to 360 for mSPHK2), which encompass domains C1 to C4, have 47% identity and 79% similarity (FIG. 1B). In the C terminal portion of the proteins there are also large homologous regions, which include the C5 domain, from amino acid 227 to 3.81 for mSPHK1 and 480 to 617 for mSPHK2, with 43% identity and 78% similarity (FIG. 1B). The divergence in these domains suggests that SPHK2 probably did not arise as a simple gene duplication event.

Tissue Distribution of Sphingosine Kinase Type 2

Figure 2A:
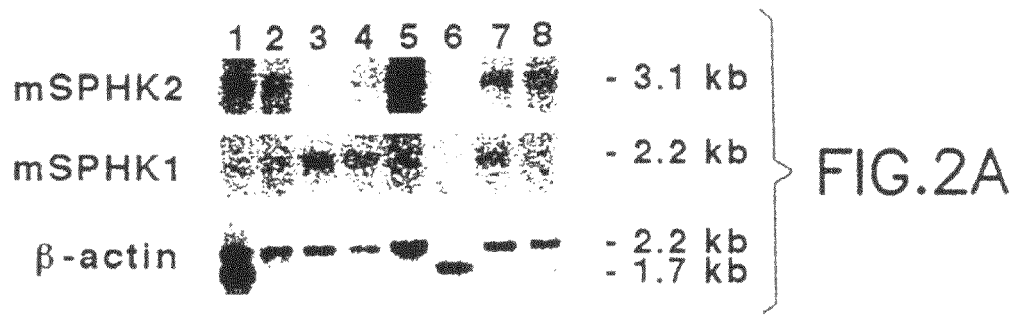
FIGS. 2A, 2B and 2C are Northern blots which show the tissue specific expression of type 1 and type 2 sphingosine kinase.
Figure 2B:
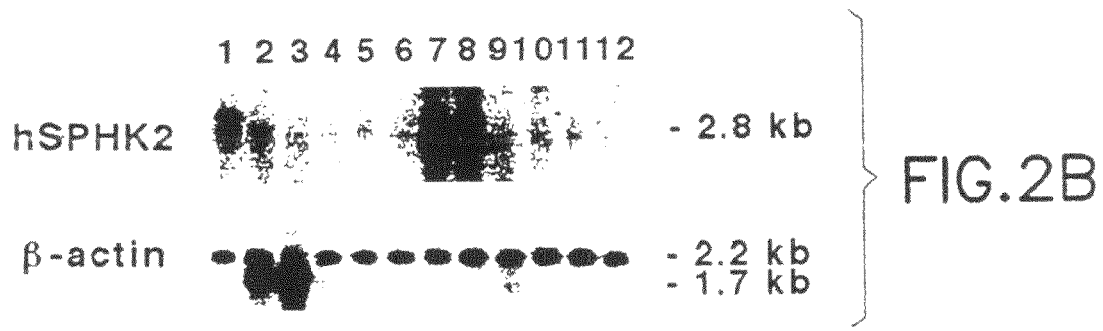
Figure 2C:

The tissue distribution of SPHK2 mRNA expression in adult mouse was compared to that of SPHK1 by Northern blotting (FIG. 2A). In most tissues, including adult liver, heart, kidney, testis and brain, a predominant 3.1 kb SPHK2 mRNA species was detected, indicating ubiquitous expression. However, the level of expression was markedly variable and was highest in adult liver and heart and barely detectable in skeletal muscle and spleen (FIG. 2A). In contrast, the expression pattern of mSPHK1 was quite different, with the highest mRNA expression in adult lung, spleen, and liver, although expression in the liver did not predominate as with mSPHK2. mSPHK1 and mSPHK2 were both temporally and differentially expressed during embryonic development. mSPHK1 was expressed highly at mouse embryonic day 7 (E7) and decreased dramatically after E11 (FIG. 2B). In contrast, at E7, mSPHK2 expression was much lower than mSPHK1, and gradually increased up to E17. The hSPHK2 2.8 kb mRNA transcript was mainly expressed in adult kidney, liver and brain, with much lower expression in other tissues (FIG. 2C). Interestingly, expression of SPHK2 in human kidney was very high and relatively much lower in the mouse, while the opposite pattern held for the liver.

Activity of Recombinant Sphingosine Kinase Type 2

Figure 3A:
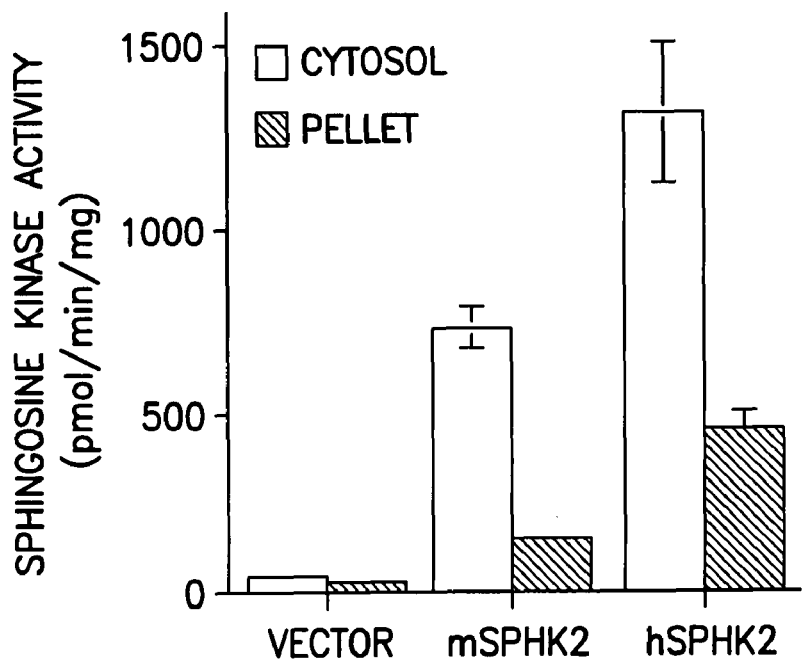
FIGS. 3A and 3B are graphs which show the enzymatic activity of recombinant SPHK2.
Figure 3B:
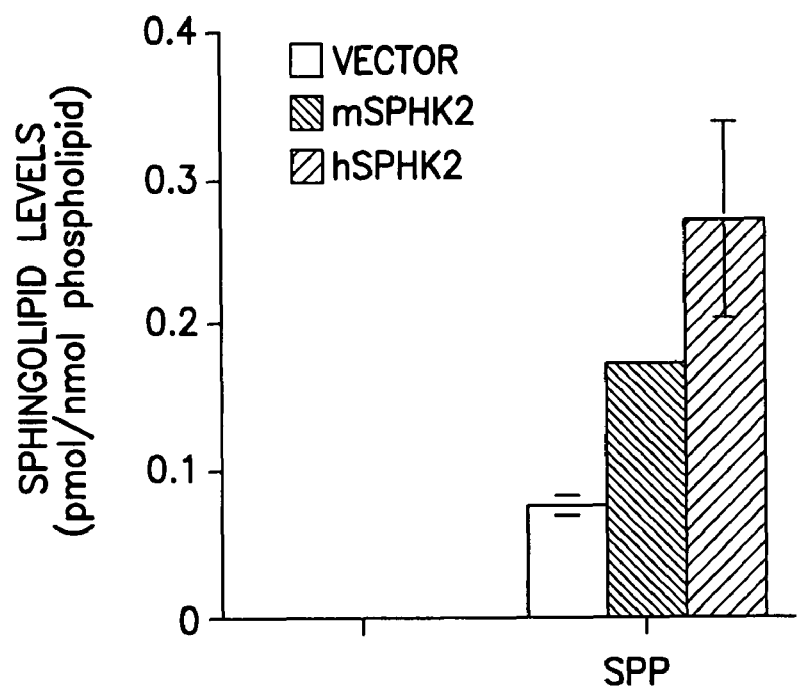

To investigate whether mSPHK2 and hSPHK2 encode bona fide SPHKs, HEK293 cells were transiently transfected with expression vectors containing the corresponding cDNAs. Because previous studies have indicated that SPHK might be present in cells in both soluble and membrane-associated forms (Olivera, A., and Spiegel, S., *Nature*, 365, (1993) 557-560; Banno, Y., Kato, M., Hara, A., and Nozawa, Y., *Biochem. J.*, 335, (1998) 301-304; Buehrer, B. M., and Bell, R. M., *J. Biol. Chem.*, 267, 3154-3159; Olivera, A. Rosenthal, J., and Spiegel, S., *Anal. Biochem.*, 223, (1994) 306-312; Ghosh, T. K., Bian, J., and Gill, D. L., *J. Biol. Chem.*, 269, (1994), 22628-22635), recombinant SPHK2 activity was measured both in cytosol and in membrane fractions of transfected cells. As previously described in Kohama, T., Olivera, A., Edsall, L., Nagiec, M. M., Dickson, R., and Spiegel, S., *J. Biol. Chem.*, 273, (1998) 23722-23728, untreated or vector transfected HEK 293 cells have low levels of SPHK activity (FIG. 3A). Twenty four hours after transfection with mSPHK2 and hSPHK2, in vitro SPHK activity was increased by 20 and 35 fold, respectively, and then decreased thereafter (FIG. 3A). In contrast, SPHK activity from cells transfected with mSPHK1 was much higher, 610-fold more than basal levels 24 hours after transfection and remaining at this level for at least 3 more days (data not shown). As in HEK293 cells, transfection of NIH 3T3 fibroblasts with mSPHK1 resulted in much higher SPHK activity than with mSPHK2. It was previously found that, similar to untransfected cells, the majority of SPHK activity in cells transfected with mSPHK1 was cytosolic (Kohama, T., Olivera, A., Edsall, L., Nagiec, M. M., Dickson, R., and Spiegel, S., *J. Biol. Chem.*, 273, (1998) 23722-23728). Similarly, in cells transfected with either mSPHK2 or hSPHK2, 17% and 26%, respectively, of the SPHK activity was membrane-associated (FIG. 3B), although Kyte-Doolittle hydropathy plots did not suggest the presence of hydrophobic membrane-spanning domains.

Transfection of HEK 293 cells with mSPHK2 and hSPHK2 also resulted in 2.2- and 3.3-fold increases in SPP, the product formed by SPHK, respectively (FIG. 3C), was in agreement with previous studies of sphingolipid metabolite levels after transfections with mSPHK1a showing a lack of correlation of fold increases in levels and in vitro enzyme activity (Kohama, T., Olivera, A., Edsall, L., Nagiec, M. M., Dickson, R., and Spiegel, S., *J. Biol. Chem.*, 273, (1998) 23722-23728; Olivera, A., Kohama, T., Edsall, L. C., Nava, V., Cuvillier, O., Poulton, S., and Spiegel, S., *J. Cell Biol.*, 147, (1999), 545-558).

Characteristics of Recombinant mSPHK2

Substrate Specificity

Figure 4A:
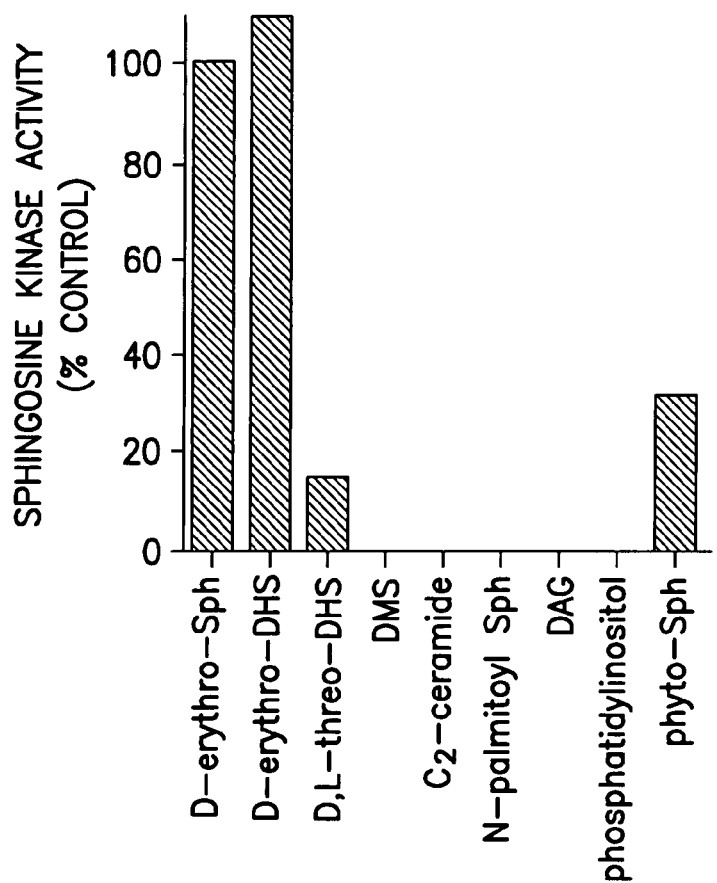
FIGS. 4A to 4D are graphs which show the substrate specificity of mSPHK2.

Although SPHK2 is highly homologous to SPHK1, there are substantial sequence differences. Therefore, it was of interest to compare their enzymatic properties. Typical Michaelis-Menten kinetics were observed for recombinant SPHK2 (data not shown). The Km for D-erythro-sphingosine as substrate is 3.4 µM, almost identical to the Km previously found for SPHK1 (Olivera, A., Kohama, T., Tu, Z., Milstien, S., and Spiegel, S., *J. Biol. Chem.*, 273, (1998), 12576-12583). Although the naturally occurring D-erythro-sphingosine isomer was the best substrate for SPHK1 (Kohama, T., Olivera, A., Edsall, L., Nagiec, M. M., Dickson, R., and Spiegel, S., *J. Biol. Chem.*, 273, (1998) 23722-23728), D-erythro-dihydrosphingosine was a better substrate for SPHK2 than D-erythro-sphingosine (FIG. 4A). Moreover, although D,L-threo-dihydrosphingosine and phytosphingosine were not phosphorylated at all by SPHK1, they were significantly phosphorylated by SPHK2, albeit much less efficiently than sphingosine. Like SPHK1, other lipids including N,N-dimethylsphingosine (DMS), C2- or C16-ceramide, diacylglycerol, and phosphatidylinositol, were not phosphorylated by SPHK2 (FIG. 6A), suggesting high specificity for the sphingoid base.

Figure 4B:
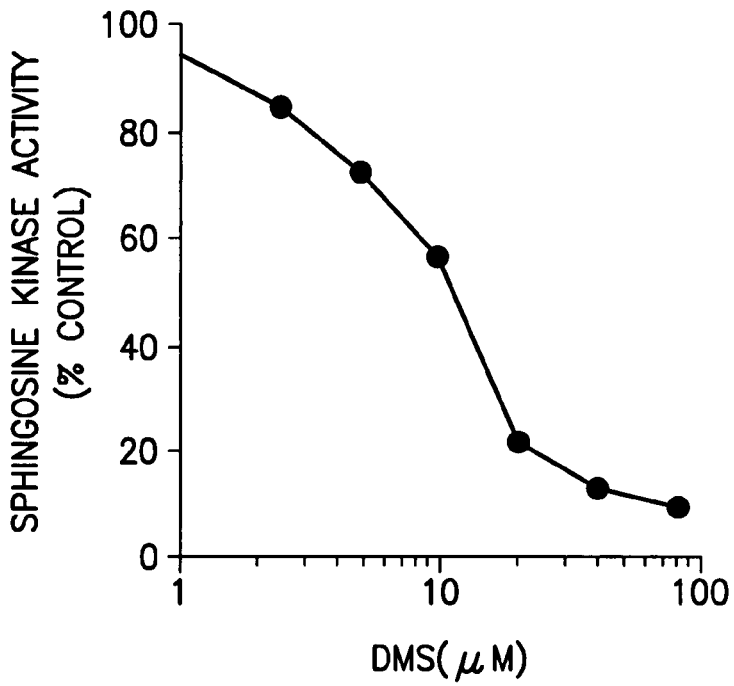
Figure 4C:
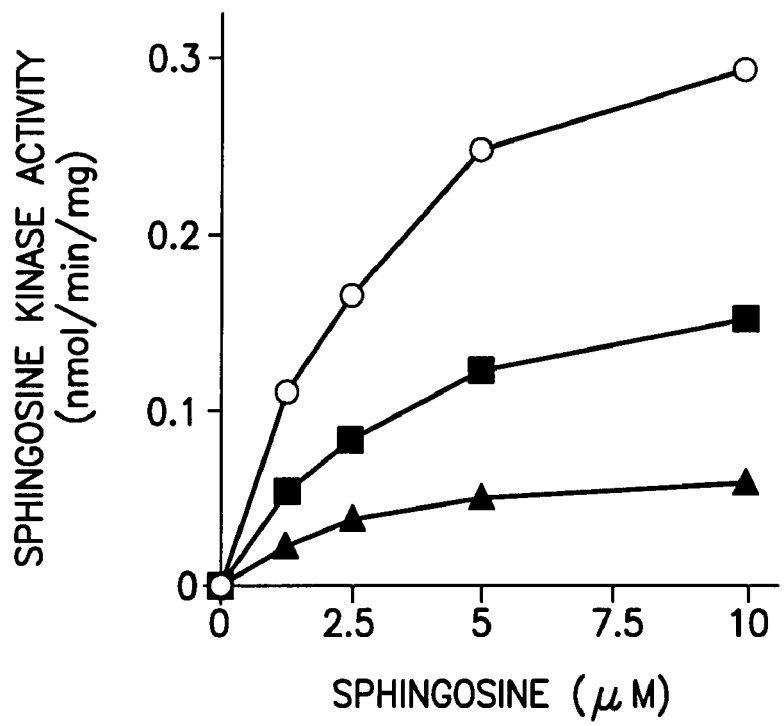
Figure 4D:
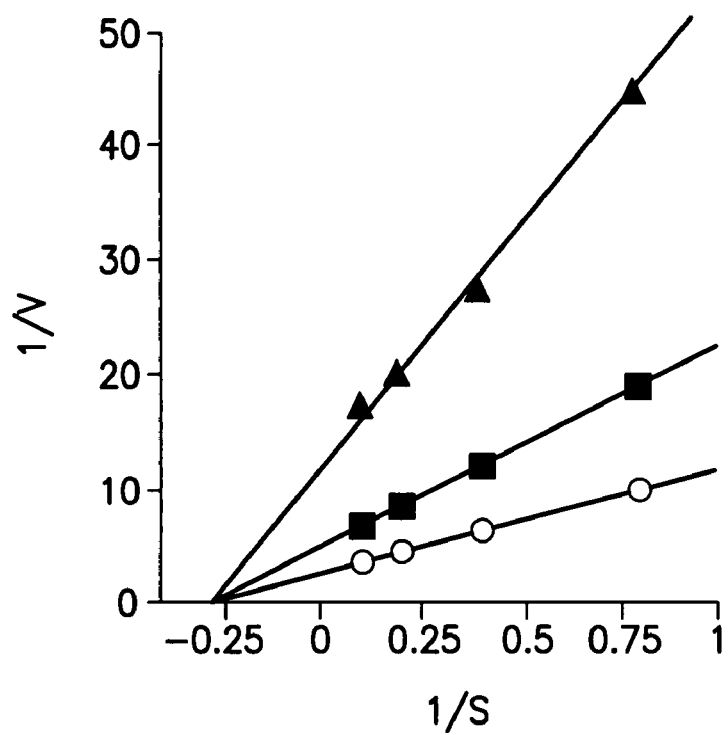
Figure 5A:
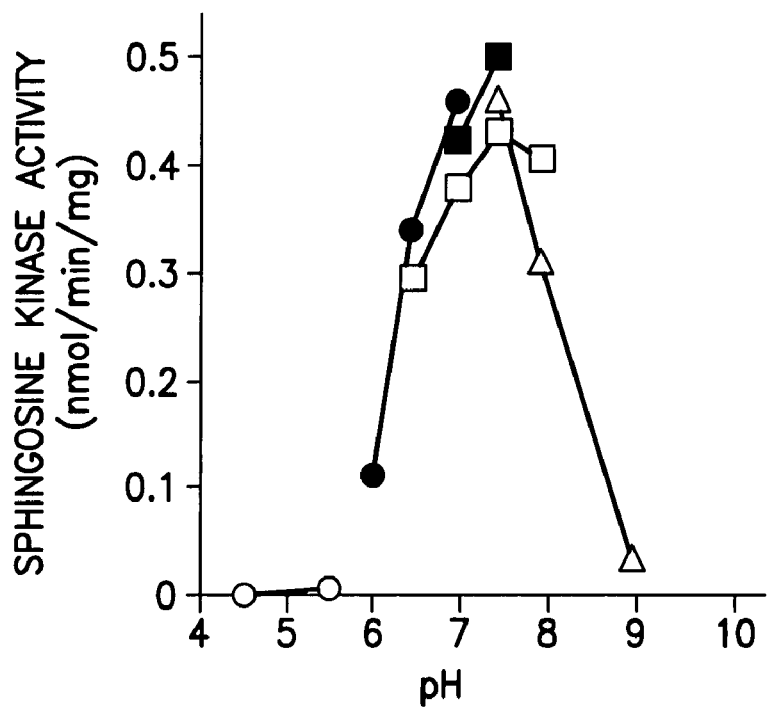
FIGS. 5A to 5E are graphs which show the pH dependence and salt effects on mSPHK2.

DMS and DHS have previously been shown to be a potent competitive inhibitors of SPHK1 (Edsall, L. C., Van Brocklyn, J. R., Cuvillier, O., Kleuser, B., and Spiegel, S., *Biochemistry*, 37, (1998), 12892-12898) and have been used to block increases in intracellular SPP levels resulting from various physiological stimuli (Olivera, A., and Spiegel, S., *Nature*, 365, (1993), 557-560; Cuvillier, O., Pirianov, G., Kleuser, B., Vanek, P. G., Coo, O. A., Gutkind, S., and Spiegel, S., *Nature*, 381, (1996), 800-803; Edsall, L. C., Pirianov, G. G., and Spiegel, S., *J. Neurosci*, 17, (1997), 6952-6960; Meyer zu Heringdorf, D., Lass, H., Alemany, R., Laser, K. T., Neumann, E., Zhang, C., Schmidt, M., Rauen, U., Jakobs, K. H., and van Koppen, C. J., *EMBO J.*, 17, 2830-2837; Choi, O, H., Kim, J.-H., and Kinet, J.-P., *Nature*, 380, (1996), 634-636; Melendez, A., Floto, R. A., Gillooly, D. J., Harnett, M. M., and Allen, J. M., *J. Biol. Chem.*, 273, 9393-9402; Machwate, M., Rodan, S. B., Rodan, G. A., and Harada, S. I., *Mol. Pharmacol.*, 54, (1998), 70-77). However, because DHS is a substrate for SPHK2 and the product, dihydro SPP, is as potent as SPP in binding to and activating cell surface SPP EDG-1 family receptors, it cannot be used as a tool to investigate the role of SPHK2. Thus, it was important to characterize the inhibitory potential of the non-substrate DMS on SPHK2. Surprisingly, it was found that although DMS was also a potent inhibitor of SPHK2 (FIG. 4B), it acted in a non-competitive manner (FIG. 4C and FIG. 4D). The Ki for DMS with SPHK2 was 12 µM, slightly higher than the Ki of 4 µM with SPHK1, making it a useful tool to inhibit both types of SPHK.

mSPHK2 had highest activity in the neutral pH range from 6.5 to 8 with optimal activity at pH 7.5 (FIG. 5A), a pH dependency similar to that of SPHK1 (data not shown). The activity decreased markedly at pH values below and above this range.

Effects of KCl and NaCl

Figure 5B:
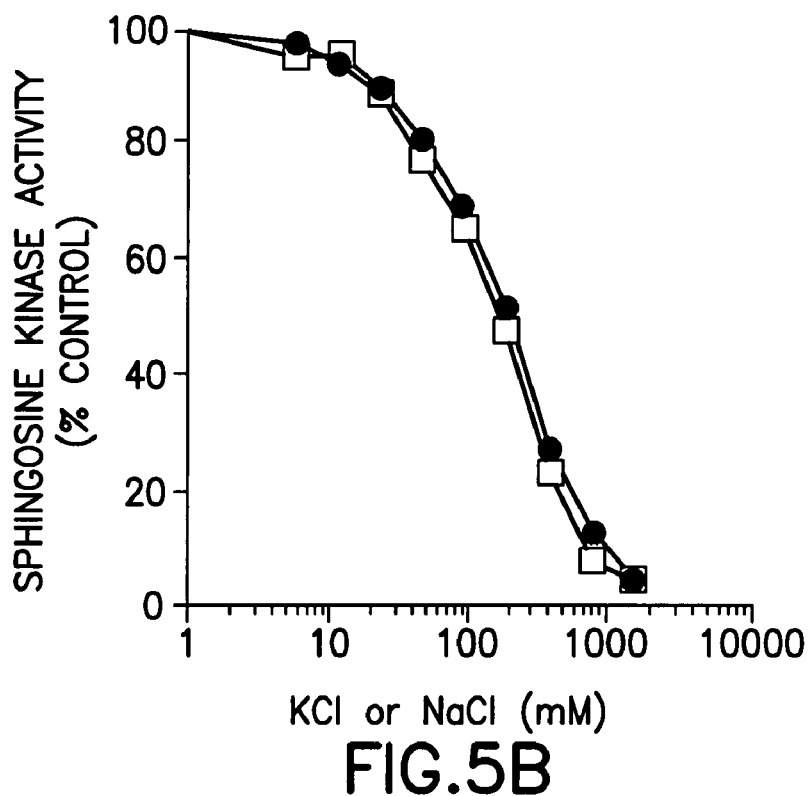
Figure 5C:
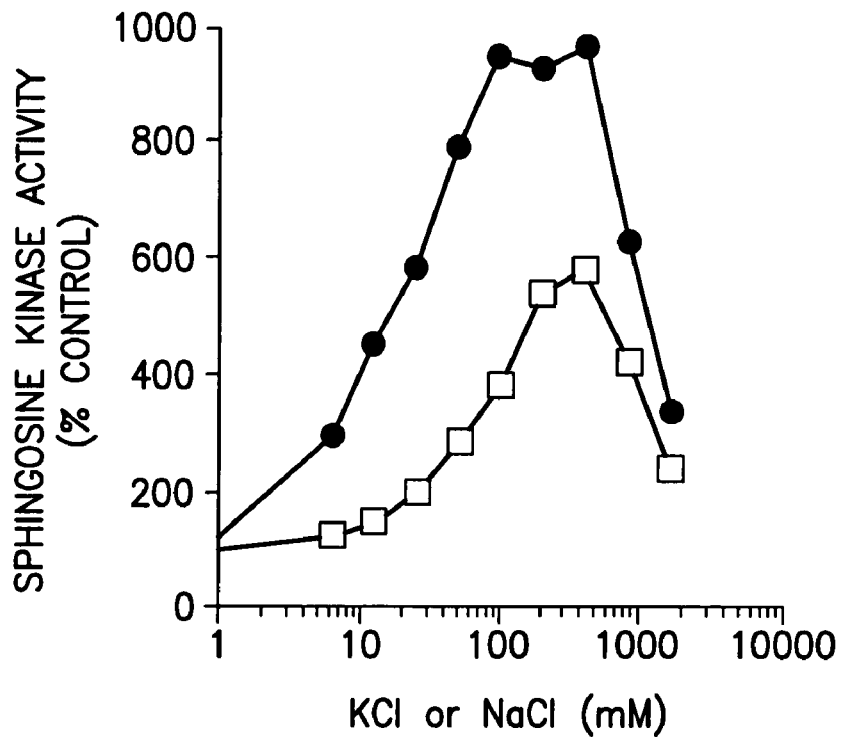
Figure 5D:
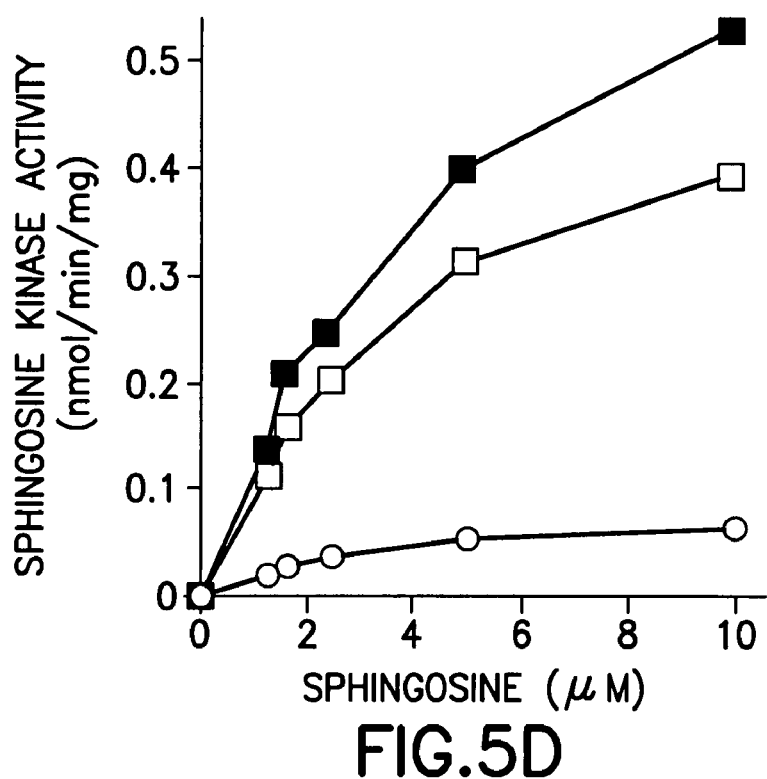
Figure 5E:
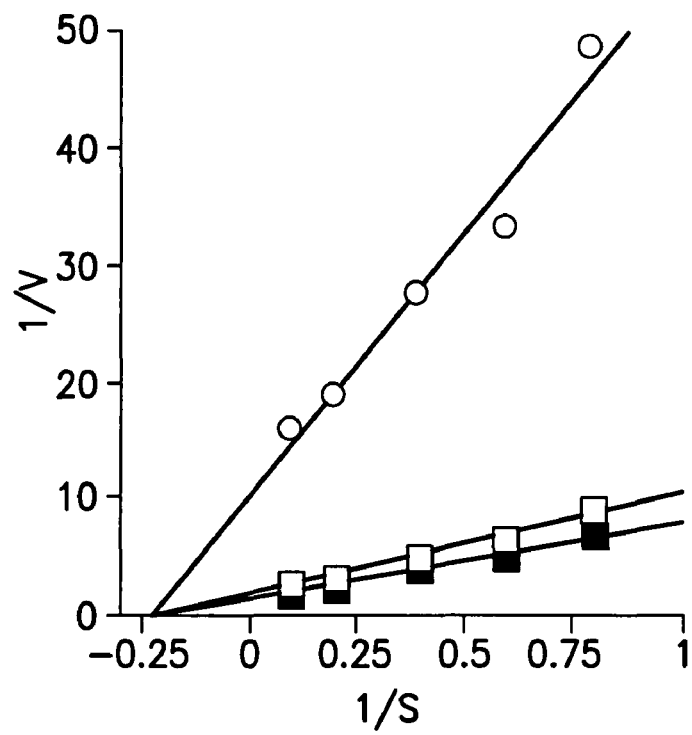

Most of the SPHK activity in human platelets is membrane-associated and extractable with 1 M NaCl (Banno, Y., Kato, M., Hara, A. and Nozawa, Y., *Biochem. J.*, 335, (1998), 301-304). Furthermore, the salt extractable SPHK from platelets has different properties than the cytosolic enzyme. It was thus of interest to determine the effect of high salt concentrations on recombinant SPHK1 and SPHK2. Interestingly, it was found that high ionic strength had completely opposite effects on their activities. SPHK1 was inhibited markedly inhibited by either NaCl and KCl with each causing 50% inhibition at a concentration of 200 mM (FIG. 5B). In contrast, SPHK2 activity was dramatically stimulated by increasing the salt concentration, with a maximal effect at a concentration of 400 mM, although KCl was much more effective than NaCl. However, above this concentration, SPHK2 activity decreased sharply although remaining elevated even at 1 M salt (FIG. 5C). Thus, the activities of SPHK1 and SPHK2 have completely opposite responses to changes in ionic strength. Kinetic analysis of mSPHK2 in the presence and absence of high concentrations of salt indicated that the Km for sphingosine was unaltered but the Vmax was increased (FIG. 5D and FIG. 5E). The physiological significance of these observations remains to be determined but it might be related to different subcellular localizations.

Substrate Presentation

Figure 6A:
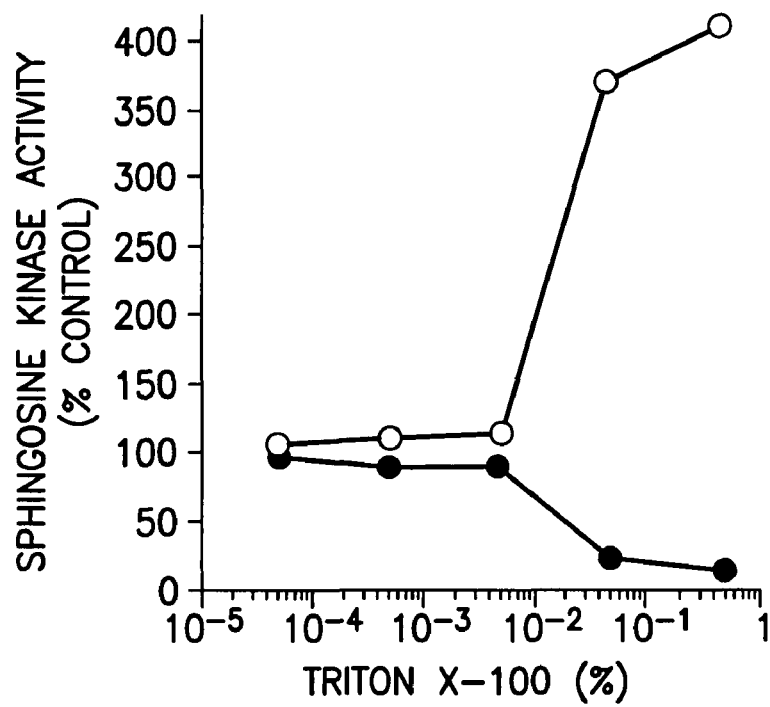
FIGS. 6A to 6B are graphs which show that Triton X-100 and bovine serum albumin ("BSA") have differential effects on the activity of SPHK1 and SPHK2. HEK293 cells were transfected with mSPHK1a (open circles) or mSPHK2 (filled circles) and the activities of each in cell lysates were measured after 24 hours in the presence of the indicated concentrations of Triton X-100 (FIG. 6A) or BSA (FIG. 6B).

Because sphingolipids are highly lipophilic, in in vitro SPHK assays, sphingosine is usually presented in micellar form with Triton X-100 or as a complex with BSA (Olivera, A., Rosenthal, J., and Spiegel, S., *J. Cell. Biochem.*, 60, (1996), 529-537; Olivera, A., Barlow, K. D., and Spiegel, S., *Methods Enzymol*, 311, (2000), 215-223). Furthermore, detergents such as Triton X-100 have been shown to stimulate the activity of SPHK in rat brain extracts (Buehrer, B. M., and Bell, R. M., *J. Biol. Chem.*, 267, (1992), 3154-3159) and the enzyme from rat kidney (Olivera, A., Kohama, T., Tu, Z., Milstien, and Spiegel, S., *J. Biol. Chem.*, 273, (1998), 12576-12583), and it was previously found that the stability of rat kidney SPHK was increased in the presence of certain detergents (Olivera, A., Kohama, T., Tu, Z., Milstien, and Spiegel, S., *J. Biol. Chem.*, 273, (1998), 12576-12583). However, when the effect of increasing concentrations of Triton X-100 on the activities of SPHK1 and SPHK2 were compared, some unexpected results were found. Concentrations of detergent below 0.005% had no effect, but at higher concentrations, SPHK2 activity was inhibited and SPHK1 activity was markedly increased (FIG. 6A). At a concentration of Triton X-100 of 0.5%, SPHK1 activity was increased by more than 4 fold while SPHK2 was almost completely inhibited.

Figure 6B:
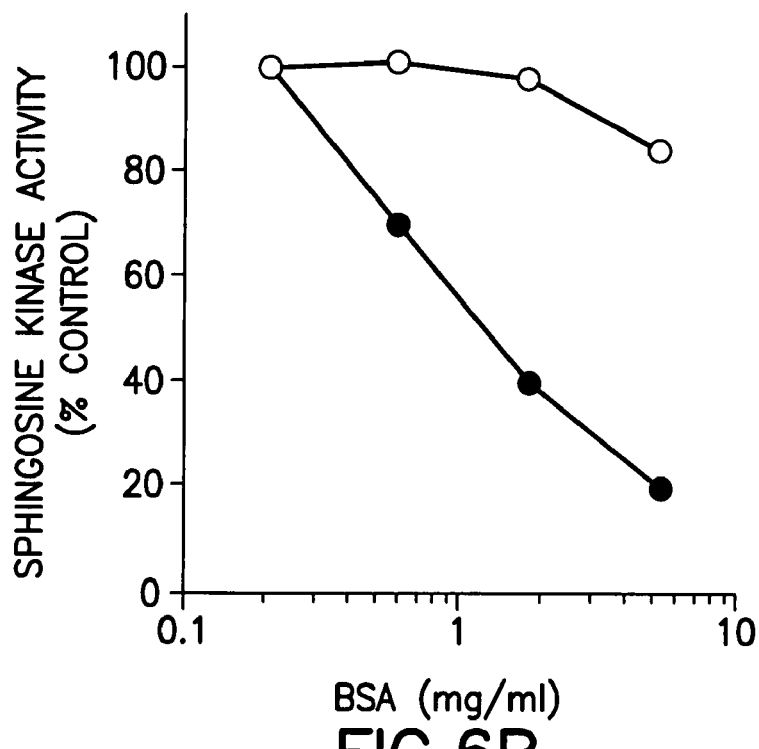

Interestingly, increasing the BSA concentration from the usual SPHK assay conditions with sphingosine-BSA complex as a substrate, i.e. 0.2 mg/ml BSA, caused a concentration-dependent inhibition of SPHK2 activity without affecting SPHK1 activity (FIG. 6B). Therefore, when measuring SPHK activity in cell or tissue extracts, the method of substrate preparation, whether in mixed micelles or in BSA complexes, must be carefully optimized because the differential effects of Triton X-100 and BSA on activity could yield different results depending on the relative expression of the two types of SPHK.

Effects of Phospholipids

Figure 6C:
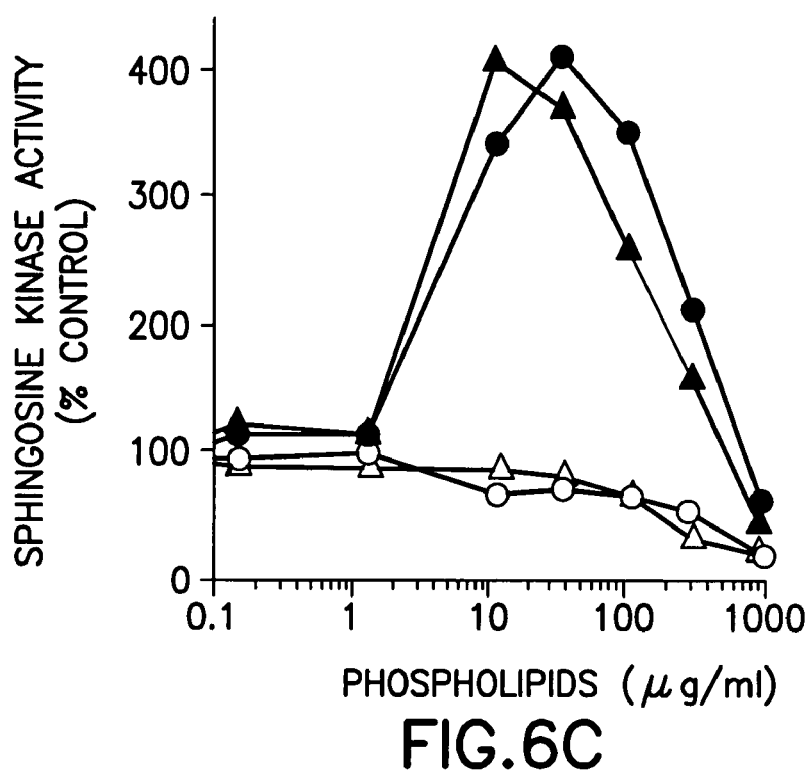
FIG. 6C is a graph which shows that phosphatidylserine has similar effects on the activity of SPHK1 and SPHK2. HEK293 cells were transfected with mSPHK1a (circles) or mSPHK2 (triangles) and the activities of each in cell lysates were measured after 24 hours in the presence of the indicated concentrations of phosphatidylserine (filled symbols) or phosphatidylcholine (open symbols). Data are expressed as percentage of control activity measured without any additions.

Acidic phospholipids, particularly phosphatidylserine, and phosphatidic acid and phosphatidylinositol, and cardiolipin to a lesser extent, induce a dose-dependent increase in SPHK activity in Swiss 3T3 fibroblast lysates, whereas neutral phospholipids had no effect (Olivera, A., Rosenthal, J., and Spiegel, S., *J. Cell. Biochem.*, 60, (1996), 529-537). In agreement, recombinant SPHK1 and SPHK2 were stimulated by phosphatidylserine; the activity of both was maximally increased 4-fold at a concentration of 40 µg/ml (FIG. 6C) and inhibited by higher concentrations in a dose-dependent manner. These effects of phosphatidylserine appeared to be specific since other phospholipids, including phosphatidylcholine, had no effect on the enzyme activity. In contrast, the activities of the three major forms of SPHK in human platelets are not affected by phosphatidylserine (Banno, Y., Kato, M., Hara, A, and Nozawa, Y., *Biochem. J.*, 335, (1998), 301-304).

The mechanism by which phosphatidylserine enhances the enzymatic activity of SPHK is not yet understood. One possibility is that phosphatidylserine possesses unique membrane-structuring properties which better present the substrate, sphingosine. A second possibility is that SPHK contains determinants that specifically recognize the structure of the serine headgroup and that these determinants may only become exposed upon interaction of SPHK with membranes. In this regard, the molecular basis for the remarkable specificity of protein kinase C for phosphatidylserine has been the subject of much debate. However, recent data reveal that lipid structure and not membrane structure is the major determinant in the regulation of protein kinase C by phosphatidylserine (Johnson, J. E., Zimmerman, M. L., Daleke, D. L., and Newton, A. C., *Biochemistry*, 37, (1998), 12020-12025).

The presence of multiple ESTs in the database with significant homologies to SPHK1 as well as the identification of several genes in *S. cerevisiae* encoding different SPHKs (Nagiec, M. M., Skrzypek, M., Nagiec, E. E., Lester, R. L., and Dickson, R. C., *J. Biol. Chem.*, 273, (1998), 19437-19442) suggests that there may be a large and important SPHK gene family. Although SPHK2 has a high degree of homology to SPHK1, especially in the previously identified conserved domains identified in type 1 SPHKs (Kohama, T., Olivera, A., Edsall, L., Nagiec, M. M., Dickson, R., and Spiegel, S., *J. Biol. Chem.*, 273, (1998), 23722-23728), it is much larger (65.2 and 65.6 kDa for SPHK1 and SPHK2, respectively versus 42.4 kDa for mSPHK1a) and contains an additional 236 amino acids. Furthermore, its differential tissue expression, temporal developmental expression, cellular localization, and kinetic properties in response to increasing ionic strength and detergents, are completely different from SPHK1, suggesting that it most likely has a different function and regulates levels of SPP in a different manner than SPHK1 which is known to play a prominent role in regulating cell growth and survival. Thus, type 2 SPHK is considered to be involved in regulation of some of the numerous biological responses attributed to SPP, such as angiogenesis and allergic responses.

(SEQ ID NO: 11)
Sequence for GenBank ® database 1 EMBC Bank Accession No. bankit325787

```
   1 aattcggcac gagggaggac cgagtaaacc gaggcttcca gaaccaaaga gaagtcagcc
  61 tgaggaaagg gctgggaccc ggagcctctc tggcctttcc ccgtccctgc tctaacactc
 121 tccagggggta aagggaccgg agaatcagag acatgatcgg agcttgctgg acgagtcgcg
 181 tggtgactct ctggccgcac gccgaccgct tctcggtggc tcgcggagga cccggtgggc
 241 tgtgtgtcgg agcctccgaa gtagctggaa tcaccgtctt tcaacacttg gcctggctct
 301 gccatttaaa gttgtgatct tggaggctgg tccaggagct gaccacaagc caagagccta
 361 ggagtgcttg ggactgaacc agggtcatgg ccccaccacc actactgcca gtggctgcca
 421 gcactccaat cctgcacggc gagtttggtt cctacccggc caacggccca cggtttgccc
 481 tcaccctcac aacacaagcc ctacacatac agcgactacg cccaaagcca gaagcccggc
 541 cccgagatgg tctagtctct ctggatgagg tctcgggctg tggcaccctg cagagccgta
 601 gccccgagga cactgcagcc tacttctgca tctacaccta cccacgtggc cgtcgagggg
 661 gccggcgcag agctacgcgg accttccggg cggatggggc caccacttat gaggagaatc
 721 gtgcagaggc ccagcgctgg gccactgccc tcacgtgtct cctccgagga gtgcctctgt
 781 cagggggacca ggaaatcacc cctgaattgc tgccccggaa gcccaggctg ctcatattgg
 841 tcaatccctt tgggggggcgg ggcctggcct ggcagcgctg tatggaccac gtggtgccaa
 901 tgatctctga agctgggctg tccttcaacc tcatacagac agaacgacag aaccatgccc
 961 gtgagctggt gcagggggtta agcctgagtg agtgggaagg cattgtcact gtgtctggag
1021 acgggctgct ttacgaggtg ctgaatgggc tccttgatcg gccagactgg gaggatgccg
1081 tgcggatgcc cattggtgtc ctcccctgtg gatcgggcaa tgcgctagct ggggcggtga
1141 gccatcatgg cgggtttgag caggttgtcg gtgttgacct gttgctcaac tgctcgcttc
1201 ttctctgccg tggtggcagc catcctctgg acttgctctc tgtgacgcta gcctcgggat
1261 cccgctgttt ttccttcctg tcagtggcct ggggattctt gtcagatgtg acattcaca
1321 gtgagcgctt cagggccctg ggcagcgctc gattcacact gggtgcagtg ctaggcctgg
1381 cctcgttgca tacctaccgt ggacgcctcc cctacctccc cgctaccaca gaaccagcct
1441 tgcccatccc aggccacagt ctgcctcgag ccaagtcaga actagtcttg gctccagccc
1501 cagcccccgc cgccacccac tgcctctac atcgatctgt gtctgacctg cccctgcccc
1561 ttccccagcc tgccttggtc tcccctggct cccctgagcc cctgcctgac ctgtccctca
1621 atggtggtgg tccagagctg actgagagact ggggaggagc tggggatgca cctctgtccc
1681 cagacccact gctgccttca tcccccaacg ctctcaaaac agctcagctt tcacccatcg
1741 ctgaagggcc cccagaaatg ccagcatctt cggggttcct gcctcccacc cacagtgccc
1801 cagaagcctc tacctggggc ccagtggacc acctcctccc tcccctgggc tctccactgc
1861 cccaagactg ggtgacaata gaggggggagt ttgtactcat gttgggcatc ttgacgagcc
1921 acctctgcgc agacctgatg gcagcccac atgcacgctt tgatgatggc gttgtgcacc
1981 tgtgttgggt gcggagcggc atctcacggg ctgcacttct acgcattttt ctggccatgg
2041 agcatggaaa ccacttcagc ctgggctgcc cccatctggg ctatgctgca gcacgtgcct
2101 tccgccttga accactcacg cctcgtggcc tgctcactgt agatggggag ttagtggagt
```

-continued

```
2161 atgggccaat acaggcgcag gtgcacccag gtctcgccac gctgctcact gggcctgcag
2221 gtcaaaagcc acaagcctga acgagcctaa aagcatggcg agttggtgga accagcgccc
2281 cataggctaa gatctatcat ttacaggtag aagtggggcc cgcactcaga actgtgagga
2341 gggtggagag tggtcctgac cctcagttcc cagaggacct agaggctcga gggtggggcc
2401 tgcctttctt gatgtccaat gatggggcct ggaatgtatg agctagcaag gcttcttcag
2461 cttattgacc agccagggtt tcttcttgcc tactccggtg cctctacttg actgccaat
2521 cagcccttga ggggcaggtt cccccaggtg gtccccagat ttgcactaat gttcctcccc
2581 tggccagtta gggatgggat gttctgtgtc ttgtgtgtcc ctctccctag tctaaaaagc
2641 aattgaaaag gtctatgcaa taaaggttgt tgcttccctc taaaaaaaaa aaaaaaa
```
(SEQ ID NO: 13)

Sequence for GenBank ® database 1 EMBC Bank Accession No. bankit325752

```
   1 gccaccatgg ccccgccccc accgccactg gctgccagca ccccgctcct ccatggcgag
  61 tttggctcct acccagcccg aggcccacgc tttgccctca cccttacatc gcaggccctg
 121 cacatacagc ggctgcgccc caaacctgaa gccaggcccc ggggtggcct ggtcccgttg
 181 gccgaggtct caggctgctg caccctgcga agccgcagcc cctcagactc agcggcctac
 241 ttctgcatct acacctaccc tcggggccgg cgcggggccc ggcgcagagc cactcgcacc
 301 ttccgggcag atggggccgc cacctacgaa gagaaccgtg ccgaggccca gcgctgggcc
 361 actgccctca cctgtctgct ccgaggactg ccactgcccg gggatgggga gatcacccct
 421 gacctgctac ctcggccgcc ccggttgctt ctattggtca atccctttgg gggtcggggc
 481 ctggcctggc agtggtgtaa gaaccacgtg cttcccatga tctctgaagc tgggctgtcc
 541 ttcaacctca tccagacaga acgacagaac cacgcccggg agctggtcca ggggctgagc
 601 ctgagtgagt gggatggcat cgtcacggtc tcgggagacg ggctgctcca tgaggtgctg
 661 aacgggctcc tagatcgccc tgactgggag gaagctgtga agatgcctgt gggcatcctc
 721 ccctgcggct cgggcaacgc gctggccgga gcagtgaacc agcacggggg atttgagcca
 781 gccctgggcc tcgacctgtt gctcaactgc tcactgttgc tgtgccgggg tggtggccac
 841 ccactggacc tgctctccgt gacgctggcc tcgggctccc gctgtttctc cttcctgtct
 901 gtggcctggg gcttcgtgtc agatgtggat atccagagcg agcgcttcag ggccttgggc
 961 agtgcccgct tcacactggg cacggtgctg ggcctcgcca cactgcacac ctaccgcgga
1021 cgcctctcct acctccccgc cactgtggaa cctgcctcgc ccacccctgc ccatagcctg
1081 cctcgtgcca agtcggagct gaccctaacc ccagacccag ccccgcccat ggcccactca
1141 ccctgcatc gttctgtgtc tgacctgcct cttcccctgc ccagcctgc cctggcctct
1201 cctggctcgc cagaacccct gcccatcctg tccctcaacg gtgggggccc agagctggct
1261 ggggactggg gtggggctgg ggatgctccg ctgtccccgg acccactgct gtcttcacct
1321 cctggctctc ccaaggcagc tctacactca cccgtctccg aaggggcccc cgtaattccc
1381 ccatcctctg ggctcccact tcccacccct gatgcccggg taggggcctc cgacctgcggc
1441 ccgcccgacc acctgctgcc tccgctgggc acccgctgc cccagactg gtgacgctg
1501 gaggggggact ttgtgctcat gttggccatc tcgcccagcc acctaggcgc tgacctggtg
1561 gcagctccgc atgcgcgctt cgacgacggc ctggtgcacc tgtgctgggt gcgtagcggc
1621 atctcgcggg ctgcgctgct gcgccttttc ttggccatgg agcgtggtag ccacttcagc
1681 ctgggctgtc cgcagctggg ctacgccgcg gccgtgcct tccgcctaga gccgctcaca
1741 ccacgcggcg tgctcacagt ggacggggag caggtggagt atgggccgct acaggcacag
```

```
1801 atgcaccctg gcatcggtac actgctcact gggcctcctg gctgcccggg gcgggagccc 1861 tgaaactaaa caagcttggt acccgccggg ggcggggcct acattccaat ggggcggagc 1921 ttgagctagg gggtgtggcc tggctgctag agttgtggtg gcaggggccc tggccccgtc 1981 tcaggattgc gctcgctttc atgggaccag acgtgatgct ggaaggtggg cgtcgtcacg 2041 gttaaagaga aatgggctcg tcccgagggt agtgcctgat caatgagggc ggggcctggc 2101 gtctgatctg gggccgccct tacggggcag ggctcagtcc tgacgcttgc cacctgctcc 2161 tacccggcca ggatggctga gggcggagtc tattttacgc gtcgcccaat gacaggacct 2221 ggaatgtact ggctggggta ggcctcagtg agtcggccgg tcagggcccg cagcctcgcc 2281 ccatccactc cggtgcctcc atttagctgg ccaatcagcc caggaggggc aggttccccg 2341 gggccggcgc taggatttgc actaatgttc ctctccccgc
```

SEQ ID NO. 14
Amino acid sequences of human SPHK2
MAPPPPPLAASTPLLHGEFGSYPARGPRFALTLTSQALHIQRLRPKPEARPRGGLVPLAEVSGCCTLRSR

SPSDSAAYFCIYTYPRGRRGARRRATRTFRADGAATYEENRAEAQRWATALTCLLRGLPLPGDGEITPDL

LPRPPRLLLLVNPFGGRGLAWQWCKNHVLPMISEAGLSFNLIQTERQNHARELVQGLSLSEWDGIVTVSG

DGLLHEVLNGLLDRPDWEEAVKMPVGILPCGSGNALAGAVNQHGGFEFPLGLDLLLNCSLLLCRGGGHPL

DLLSVTLASGSRCFSFLSVAWGFVSDVDIQSERFRALGSARFTLGTVLGLATLHTYRGRLSYLPATVEPA

SPTPAHSLPRAKSELTLTPDPAPPMAHSPLHRSVSDLPLPLPQPALASPGSPEPLPILSLNGGGPELAGD

WGGAGDAPLSPDPLLSSPPGSPKAALHSPVSEGAPVIPPSSGLPLPTPDARVGASTCGPPDHLLPPLGTP

LPPDWVTLEGDFVLMLAISPSHLGADLVAAPHARFDDGLVHLCWVRSGISRAALLRLFLAMERGSHFSLG

CPQLGYAAARAFRLEPLTPRGVLTVDGEQVEYGPLQAQMHPGIGTLLTGPPGCPGREP

SEQ ID NO. 12
Amino Acid Sequence of mouse SPHK2
MAPPPLLPVAASTPILHGEFGSYPANGPRFALTLTTQALHIQRLRPKPEARPRDGLVSLDEVSGCGTLQS

RSPEDTAAYFCIYTYPRGRRGGRRRATRTFRADGATTYEENRAEAQRWATALTCLLRGVPLSGDQEITPE

LLPRKPRLLILVNPFGGRGLAWQRCMDHVVPMISEAGLSFNLIQTERQNHARELVQGLSLSEWEGIVTVS

GDGLLYEVLNGLLDRPDWEDAVRMPIGVLPCGSGNALAGAVSHHGGFEQVVGVDLLLNCSLLLCRGGSHP

LDLLSVTLASGSRCFSFLSVAWGFLSDVDIHSERFRALGSARFTLGAVLGLASLHTYRGRLSYLPATTEP

ALPIPGHSLPRAKSELVLAPAPAPAATHSPLHRSVSDLPLPLPQPALVSPGSPEPLPDLSLNGGGPELTG

DWGGAGDAPLSPDPLLPSSPNALKTAQLSPIAEGPPEMPASSGFLPPTHSAPEASTWGPVDHLLPPLGSP

LPQDWVTIEGEFVLMLGILTSHLCADLMAAPHARFDDGVVHLCWVRSGISRAALLRIFLAMEHGNHFSLG

CPHLGYAAARAFRLEPLTPRGLLTVDGELVEYGPIQAQVHPGLATLLTGPAGQKPQA

It will be appreciated that the instant specification is set forth by way of illustration and not limitation, and that various modifications and changes may be made without departing from the spirit and scope of the present invention.

---

What is claimed is:

1. An isolated protein selected from the group consisting of (a) a protein having an amino acid sequence consisting essentially of SEQ ID NO: 14 and (b) a protein encoded by a nucleotide sequence consisting essentially of SEQ ID NO: 13.

2. A method of regulating a biological process selected from the group consisting of mitogenesis, apoptosis, neuronal development, chemotaxis, angiogenesis and an inflammatory response in a mammal comprising administering to a mammal in need thereof a pharmaceutically effective amount of the protein according to claim 1.

3. The method of claim 2, wherein the mammal is a human.

4. The method of claim 3, wherein the biological process is angiogenesis.

5. A method for the treatment or amelioration of a disease resulting from increased cell death or decreased cell proliferation, comprising administering to a mammal in need thereof a pharmaceutically effective amount of a protein according to claim 1.

6. The method of claim 5, wherein the mammal is a human.

7. A composition for treating or ameliorating a disease resulting from increased cell death or decreased cell proliferation comprising a pharmaceutically effective amount of a protein according to claim 1, and a pharmaceutically acceptable carrier.

8. A method for the treatment or amelioration of developmental retardation in a human comprising administering to a human in need thereof a pharmaceutically effective amount of the protein according to claim 1.

9. A method for detecting an agent or a drug which inhibits or promotes an enzymatic activity of human sphingosine kinase type 2 isoform comprising:
   (i) contacting a human sphingosine kinase type 2 isoform protein according to claim 1 and lipids in the presence of at least one drug or agent;
   (ii) detecting whether or not said drug or agent inhibits or promotes the enzymatic activity of the sphingosine kinase type 2 isoform by measuring sphingosine kinase type 2-dependent phosphorylation of the lipids and comparing the resultant measurement to a control which did not receive the drug or agent, wherein a decrease in the amount of sphingosine kinase type 2-dependent phosphorylation of the lipids as compared to the control indicates an inhibitory drug or agent, or an increase in the amount of sphingosine kinase type 2-dependent phosphorylation of the lipids as compared to the control indicates a stimulatory drug or agent.

10. A method for the treatment or amelioration of a disease resulting from decreased cell death or increased cell proliferation comprising administering to a mammal in need thereof a pharmaceutically effective amount of an antibody to a protein according to claim 1.

11. The method of claim 10, wherein the mammal is a human.

12. A method for the treatment or amelioration of a disease resulting from abnormal migration or motility of cells selected from the group consisting of cancer, restenosis and diabetic neuropathy, the method comprising administering to a mammal in need thereof, a pharmaceutically effective amount of an antibody to a protein according to claim 1.

13. The method of claim 12, wherein the mammal is a human.

14. The method according to claim 9, wherein in step (i), said human sphingosine kinase type 2 isoform protein is produced by a host cell having a recombinant vector comprising a polynucleotide having the nucleotide sequence of SEQ ID NO:13.

15. The method according to claim 9, wherein said lipids comprise at least one of D, L-threo-dihydrosphingosine and phytosphingosine.

* * * * *

SEQUENCE LISTING

<160> NUMBER OF SEQ ID NOS: 15

<210> SEQ ID NO 1
<211> LENGTH: 26
<212> TYPE: DNA
<213> ORGANISM: Mus musculus

<400> SEQUENCE: 1

```
cctgggtgca cctgcgcctg tattgg                                            26

<210> SEQ ID NO 2
<211> LENGTH: 24
<212> TYPE: DNA
<213> ORGANISM: Mus musculus

<400> SEQUENCE: 2
ccagtcttgg ggcagtggag agcc                                              24

<210> SEQ ID NO 3
<211> LENGTH: 16
<212> TYPE: DNA
<213> ORGANISM: Mus musculus

<400> SEQUENCE: 3
aggtagaggc ttctgg                                                       16

<210> SEQ ID NO 4
<211> LENGTH: 36
<212> TYPE: DNA
<213> ORGANISM: Artificial Sequence
<220> FEATURE:
<223> OTHER INFORMATION: Description of Artificial Sequence: 5'RACE
      Abridged Anchor Primer
<221> NAME/KEY: modified_base
<222> LOCATION: (24)..(25)
<223> OTHER INFORMATION: i
<221> NAME/KEY: modified_base
<222> LOCATION: (29)..(30)
<223> OTHER INFORMATION: i
<221> NAME/KEY: modified_base
<222> LOCATION: (34)..(35)
<223> OTHER INFORMATION: i

<400> SEQUENCE: 4
ggccacgcgt cgactagtac gggnngggnn gggnng                                 36

<210> SEQ ID NO 5
<211> LENGTH: 22
<212> TYPE: DNA
<213> ORGANISM: Mus musculus

<400> SEQUENCE: 5
gcgatgggtg aaagctgagc tg                                                22

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Abridged
      Universal Amplification Primer

<400> SEQUENCE: 6
ggccacgcgt cgactagtac                                                   20

<210> SEQ ID NO 7
<211> LENGTH: 22
<212> TYPE: DNA
<213> ORGANISM: Mus musculus

<400> SEQUENCE: 7
agtctccagt cagctctgga cc                                                22
```

```
<210> SEQ ID NO 8
<211> LENGTH: 16
<212> TYPE: DNA
<213> ORGANISM: Homo sapiens

<400> SEQUENCE: 8
cccactcact caggct                                                     16

<210> SEQ ID NO 9
<211> LENGTH: 22
<212> TYPE: DNA
<213> ORGANISM: Homo sapiens

<400> SEQUENCE: 9
gaaggacagc ccagcttcag ag                                              22

<210> SEQ ID NO 10
<211> LENGTH: 20
<212> TYPE: DNA
<213> ORGANISM: Homo sapiens

<400> SEQUENCE: 10
attgaccaat agaagcaacc                                                 20

<210> SEQ ID NO 11
<211> LENGTH: 2698
<212> TYPE: DNA
<213> ORGANISM: Mus musculus
<220> FEATURE:
<221> NAME/KEY: CDS
<222> LOCATION: (387)..(2237)
<300> PUBLICATION INFORMATION:
<302> TITLE: Molecular cloning and functional characterization of a
      novel mammalian sphingosine kinase type 2 isoform
<303> JOURNAL: J. Biol. Chem.
<304> VOLUME: 275
<305> ISSUE: 26
<306> PAGES: 19513-19520
<307> DATE: 2000-06-30
<308> DATABASE ACCESSION NUMBER: AF245448
<309> DATABASE ENTRY DATE: 2000-06-27

<400> SEQUENCE: 11
aattcggcac gagggaggac cgagtaaacc gaggcttcca gaaccaaaga gaagtcagcc     60
tgaggaaagg gctgggaccc ggagcctctc tggcctttcc ccgtccctgc tctaacactc    120 tccagggta aagggaccgg agaatcagag acatgatcgg agcttgctgg acgagtcgcg    180
tggtgactct ctggccgcac gccgaccgct tctcggtggc tcgcgaggga cccggtgggc    240
tgtgtgtcgg agcctccgaa gtagctggaa tcaccgtctt tcaacacttg gcctggctct    300
gccatttaaa gttgtgatct tggaggctgg tccaggagct gaccacaagc caagagccta    360
ggagtgcttg ggactgaacc agggtc atg gcc cca cca cca cta ctg cca gtg     413
                              Met Ala Pro Pro Pro Leu Leu Pro Val
                                 1               5 gct gcc agc act cca atc ctg cac ggc gag ttt ggt tcc tac ccg gcc     461
Ala Ala Ser Thr Pro Ile Leu His Gly Glu Phe Gly Ser Tyr Pro Ala
 10              15                  20                  25 aac ggc cca cgg ttt gcc ctc acc ctc aca aca caa gcc cta cac ata     509
Asn Gly Pro Arg Phe Ala Leu Thr Leu Thr Thr Gln Ala Leu His Ile
             30                  35                  40 cag cga cta cgc cca aag cca gaa gcc cgg ccc cga gat ggt cta gtc     557
Gln Arg Leu Arg Pro Lys Pro Glu Ala Arg Pro Arg Asp Gly Leu Val
         45                  50                  55 tct ctg gat gag gtc tcg ggc tgt ggc acc ctg cag agc cgt agc ccc     605
```

|     |     |     |     |     |     |     |     |     |     |     |     |     |     |     |     |      |
| --- | --- | --- | --- | --- | --- | --- | --- | --- | --- | --- | --- | --- | --- | --- | --- | ---  |
|     |     | Ser | Leu | Asp | Glu | Val | Ser | Gly | Cys | Gly | Thr | Leu | Gln | Ser | Arg | Ser | Pro  |
|     |     |     |     | 60  |     |     |     |     | 65  |     |     |     |     | 70  |     |     |      |

```
gag gac act gca gcc tac ttc tgc atc tac acc tac cca cgt ggc cgt    653
Glu Asp Thr Ala Ala Tyr Phe Cys Ile Tyr Thr Tyr Pro Arg Gly Arg
     75              80                  85 cga ggg ggc cgg cgc aga gct acg cgg acc ttc cgg gcg gat ggg gcc    701
Arg Gly Gly Arg Arg Arg Ala Thr Arg Thr Phe Arg Ala Asp Gly Ala
 90              95                 100                 105 acc act tat gag gag aat cgt gca gag gcc cag cgc tgg gcc act gcc    749
Thr Thr Tyr Glu Glu Asn Arg Ala Glu Ala Gln Arg Trp Ala Thr Ala
                110                 115                 120 ctc acg tgt ctc ctc cga gga gtg cct ctg tca ggg gac cag gaa atc    797
Leu Thr Cys Leu Leu Arg Gly Val Pro Leu Ser Gly Asp Gln Glu Ile
            125                 130                 135 acc cct gaa ttg ctg ccc cgg aag ccc agg ctg ctc ata ttg gtc aat    845
Thr Pro Glu Leu Leu Pro Arg Lys Pro Arg Leu Leu Ile Leu Val Asn
        140                 145                 150 ccc ttt ggg ggg cgg ggc ctg gcc tgg cag cgc tgt atg gac cac gtg    893
Pro Phe Gly Gly Arg Gly Leu Ala Trp Gln Arg Cys Met Asp His Val
    155                 160                 165 gtg cca atg atc tct gaa gct ggg ctg tcc ttc aac ctc ata cag aca    941
Val Pro Met Ile Ser Glu Ala Gly Leu Ser Phe Asn Leu Ile Gln Thr
170                 175                 180                 185 gaa cga cag aac cat gcc cgt gag ctg gtg cag ggg tta agc ctg agt    989
Glu Arg Gln Asn His Ala Arg Glu Leu Val Gln Gly Leu Ser Leu Ser
                190                 195                 200 gag tgg gaa ggc att gtc act gtg tct gga gac ggg ctg ctt tac gag   1037
Glu Trp Glu Gly Ile Val Thr Val Ser Gly Asp Gly Leu Leu Tyr Glu
            205                 210                 215 gtg ctg aat ggg ctc ctt gat cgg cca gac tgg gag gat gcc gtg cgg   1085
Val Leu Asn Gly Leu Leu Asp Arg Pro Asp Trp Glu Asp Ala Val Arg
        220                 225                 230 atg ccc att ggt gtc ctc ccc tgt gga tcg ggc aat gcg cta gct ggg   1133
Met Pro Ile Gly Val Leu Pro Cys Gly Ser Gly Asn Ala Leu Ala Gly
    235                 240                 245 gcg gtg agc cat cat ggc ggg ttt gag cag gtt gtc ggt gtt gac ctg   1181
Ala Val Ser His His Gly Gly Phe Glu Gln Val Val Gly Val Asp Leu
250                 255                 260                 265 ttg ctc aac tgc tcg ctt ctt ctc tgc cgt ggt ggc agc cat cct ctg   1229
Leu Leu Asn Cys Ser Leu Leu Leu Cys Arg Gly Gly Ser His Pro Leu
                270                 275                 280 gac ttg ctc tct gtg acg cta gcc tcg gga tcc cgc tgt ttt tcc ttc   1277
Asp Leu Leu Ser Val Thr Leu Ala Ser Gly Ser Arg Cys Phe Ser Phe
            285                 290                 295 ctg tca gtg gcc tgg gga ttc ttg tca gat gtg gac att cac agt gag   1325
Leu Ser Val Ala Trp Gly Phe Leu Ser Asp Val Asp Ile His Ser Glu
        300                 305                 310 cgc ttc agg gcc ctg ggc agc gct cga ttc aca ctg ggt gca gtg cta   1373
Arg Phe Arg Ala Leu Gly Ser Ala Arg Phe Thr Leu Gly Ala Val Leu
    315                 320                 325 ggc ctg gcc tcg ttg cat acc tac cgt gga cgc ctc tcc tac ctc ccc   1421
Gly Leu Ala Ser Leu His Thr Tyr Arg Gly Arg Leu Ser Tyr Leu Pro
330                 335                 340                 345 gct acc aca gaa cca gcc ttg ccc atc cca ggc cac agt ctg cct cga   1469
Ala Thr Thr Glu Pro Ala Leu Pro Ile Pro Gly His Ser Leu Pro Arg
                350                 355                 360 gcc aag tca gaa cta gtc ttg gct cca gcc cca gcc ccc gcc gcc acc   1517
Ala Lys Ser Glu Leu Val Leu Ala Pro Ala Pro Ala Pro Ala Ala Thr
            365                 370                 375
```

-continued

```
cac tcg cct cta cat cga tct gtg tct gac ctg ccc ctg ccc ctt ccc      1565
His Ser Pro Leu His Arg Ser Val Ser Asp Leu Pro Leu Pro Leu Pro
        380                 385                 390 cag cct gcc ttg gtc tcc cct ggc tcc cct gag ccc ctg cct gac ctg      1613
Gln Pro Ala Leu Val Ser Pro Gly Ser Pro Glu Pro Leu Pro Asp Leu
395                 400                 405 tcc ctc aat ggt ggt ggt cca gag ctg act gga gac tgg gga gga gct      1661
Ser Leu Asn Gly Gly Gly Pro Glu Leu Thr Gly Asp Trp Gly Gly Ala
410                 415                 420                 425 ggg gat gca cct ctg tcc cca gac cca ctg ctg cct tca tcc ccc aac      1709
Gly Asp Ala Pro Leu Ser Pro Asp Pro Leu Leu Pro Ser Ser Pro Asn
                430                 435                 440 gct ctc aaa aca gct cag ctt tca ccc atc gct gaa ggg ccc cca gaa      1757
Ala Leu Lys Thr Ala Gln Leu Ser Pro Ile Ala Glu Gly Pro Pro Glu
            445                 450                 455 atg cca gca tct tcg ggg ttc ctg cct ccc acc cac agt gcc cca gaa      1805
Met Pro Ala Ser Ser Gly Phe Leu Pro Pro Thr His Ser Ala Pro Glu
        460                 465                 470 gcc tct acc tgg ggc cca gtg gac cac ctc ctc cct ccc ctg ggc tct      1853
Ala Ser Thr Trp Gly Pro Val Asp His Leu Leu Pro Pro Leu Gly Ser
475                 480                 485 cca ctg ccc caa gac tgg gtg aca ata gag ggg gag ttt gta ctc atg      1901
Pro Leu Pro Gln Asp Trp Val Thr Ile Glu Gly Glu Phe Val Leu Met
490                 495                 500                 505 ttg ggc atc ttg acg agc cac ctc tgc gca gac ctg atg gca gcc cca      1949
Leu Gly Ile Leu Thr Ser His Leu Cys Ala Asp Leu Met Ala Ala Pro
                510                 515                 520 cat gca cgc ttt gat gat ggc gtt gtg cac ctg tgt tgg gtg cgg agc      1997
His Ala Arg Phe Asp Asp Gly Val Val His Leu Cys Trp Val Arg Ser
            525                 530                 535 ggc atc tca cgg gct gca ctt cta cgc att ttt ctg gcc atg gag cat      2045
Gly Ile Ser Arg Ala Ala Leu Leu Arg Ile Phe Leu Ala Met Glu His
        540                 545                 550 gga aac cac ttc agc ctg ggc tgc ccc cat ctg ggc tat gct gca gca      2093
Gly Asn His Phe Ser Leu Gly Cys Pro His Leu Gly Tyr Ala Ala Ala
555                 560                 565 cgt gcc ttc cgc ctt gaa cca ctc acg cct cgt ggc ctg ctc act gta      2141
Arg Ala Phe Arg Leu Glu Pro Leu Thr Pro Arg Gly Leu Leu Thr Val
570                 575                 580                 585 gat ggg gag tta gtg gag tat ggg cca ata cag gcg cag gtg cac cca      2189
Asp Gly Glu Leu Val Glu Tyr Gly Pro Ile Gln Ala Gln Val His Pro
                590                 595                 600 ggt ctc gcc acg ctg ctc act ggg cct gca ggt caa aag cca caa gcc      2237
Gly Leu Ala Thr Leu Leu Thr Gly Pro Ala Gly Gln Lys Pro Gln Ala
            605                 610                 615 tgaacgagcc taaaagcatg gcgagttggt ggaaccagcg ccccataggc taagatctat    2297
catttacagg tagaagtggg gcccgcactc agaactgtga ggagggtgga gagtggtcct    2357
gaccctcagt tcccagagga cctagaggct cgagggtggg gcctgccttt cttgatgtcc    2417
aatgatgggg cctggaatgt atgagctagc aaggcttctt cagcttattg accagccagg    2477
gtttcttctt gcctactccg gtgcctctac ttgactggcc aatcagccct tgaggggcag    2537
gttcccccag gtggtcccca gatttgcact aatgttcctc ccctggccag ttagggatgg    2597
gatgttctgt gtcttgtgtg tccctctccc tagtctaaaa agcaattgaa aaggtctatg    2657
caataaaggt tgttgcttcc ctctaaaaaa aaaaaaaaaa a                        2698
```

<210> SEQ ID NO 12
<211> LENGTH: 617

```
<212> TYPE: PRT
<213> ORGANISM: Mus musculus

<400> SEQUENCE: 12

Met Ala Pro Pro Leu Leu Pro Val Ala Ser Thr Pro Ile Leu
 1               5                  10                  15

His Gly Glu Phe Gly Ser Tyr Pro Ala Asn Gly Pro Arg Phe Ala Leu
            20                  25                  30

Thr Leu Thr Thr Gln Ala Leu His Ile Gln Arg Leu Arg Pro Lys Pro
        35                  40                  45

Glu Ala Arg Pro Arg Asp Gly Leu Val Ser Leu Asp Glu Val Ser Gly
 50                  55                  60

Cys Gly Thr Leu Gln Ser Arg Ser Pro Glu Asp Thr Ala Ala Tyr Phe
 65                  70                  75                  80

Cys Ile Tyr Thr Tyr Pro Arg Gly Arg Gly Gly Arg Arg Arg Ala
                85                  90                  95

Thr Arg Thr Phe Arg Ala Asp Gly Ala Thr Thr Tyr Glu Glu Asn Arg
            100                 105                 110

Ala Glu Ala Gln Arg Trp Ala Thr Ala Leu Thr Cys Leu Leu Arg Gly
        115                 120                 125

Val Pro Leu Ser Gly Asp Gln Glu Ile Thr Pro Glu Leu Leu Pro Arg
130                 135                 140

Lys Pro Arg Leu Leu Ile Leu Val Asn Pro Phe Gly Gly Arg Gly Leu
145                 150                 155                 160

Ala Trp Gln Arg Cys Met Asp His Val Val Pro Met Ile Ser Glu Ala
                165                 170                 175

Gly Leu Ser Phe Asn Leu Ile Gln Thr Glu Arg Gln Asn His Ala Arg
            180                 185                 190

Glu Leu Val Gln Gly Leu Ser Leu Ser Glu Trp Glu Gly Ile Val Thr
        195                 200                 205

Val Ser Gly Asp Gly Leu Leu Tyr Glu Val Leu Asn Gly Leu Leu Asp
210                 215                 220

Arg Pro Asp Trp Glu Asp Ala Val Arg Met Pro Ile Gly Val Leu Pro
225                 230                 235                 240

Cys Gly Ser Gly Asn Ala Leu Ala Gly Ala Val Ser His His Gly Gly
                245                 250                 255

Phe Glu Gln Val Val Gly Val Asp Leu Leu Leu Asn Cys Ser Leu Leu
            260                 265                 270

Leu Cys Arg Gly Gly Ser His Pro Leu Asp Leu Ser Val Thr Leu
        275                 280                 285

Ala Ser Gly Ser Arg Cys Phe Ser Phe Leu Ser Val Ala Trp Gly Phe
290                 295                 300

Leu Ser Asp Val Asp Ile His Ser Glu Arg Phe Arg Ala Leu Gly Ser
305                 310                 315                 320

Ala Arg Phe Thr Leu Gly Ala Val Leu Gly Leu Ala Ser Leu His Thr
                325                 330                 335

Tyr Arg Gly Arg Leu Ser Tyr Leu Pro Ala Thr Thr Glu Pro Ala Leu
            340                 345                 350

Pro Ile Pro Gly His Ser Leu Pro Arg Ala Lys Ser Glu Leu Val Leu
        355                 360                 365

Ala Pro Ala Pro Ala Pro Ala Thr His Ser Pro Leu His Arg Ser
370                 375                 380

Val Ser Asp Leu Pro Leu Pro Leu Pro Gln Pro Ala Leu Val Ser Pro
385                 390                 395                 400
```

-continued

Gly Ser Pro Glu Pro Leu Pro Asp Leu Ser Leu Asn Gly Gly Pro
            405                 410                 415

Glu Leu Thr Gly Asp Trp Gly Ala Gly Asp Ala Pro Leu Ser Pro
            420                 425                 430

Asp Pro Leu Leu Pro Ser Ser Pro Asn Ala Leu Lys Thr Ala Gln Leu
            435                 440                 445

Ser Pro Ile Ala Glu Gly Pro Pro Glu Met Pro Ala Ser Ser Gly Phe
    450                 455                 460

Leu Pro Pro Thr His Ser Ala Pro Glu Ala Ser Thr Trp Gly Pro Val
465                 470                 475                 480

Asp His Leu Leu Pro Pro Leu Gly Ser Pro Leu Pro Gln Asp Trp Val
                485                 490                 495

Thr Ile Glu Gly Glu Phe Val Leu Met Leu Gly Ile Leu Thr Ser His
            500                 505                 510

Leu Cys Ala Asp Leu Met Ala Ala Pro His Ala Arg Phe Asp Asp Gly
515                 520                 525

Val Val His Leu Cys Trp Val Arg Ser Gly Ile Ser Arg Ala Ala Leu
    530                 535                 540

Leu Arg Ile Phe Leu Ala Met Glu His Gly Asn His Phe Ser Leu Gly
545                 550                 555                 560

Cys Pro His Leu Gly Tyr Ala Ala Ala Arg Ala Phe Arg Leu Glu Pro
                565                 570                 575

Leu Thr Pro Arg Gly Leu Leu Thr Val Asp Gly Glu Leu Val Glu Tyr
            580                 585                 590

Gly Pro Ile Gln Ala Gln Val His Pro Gly Leu Ala Thr Leu Leu Thr
        595                 600                 605

Gly Pro Ala Gly Gln Lys Pro Gln Ala
    610                 615

<210> SEQ ID NO 13
<211> LENGTH: 2380
<212> TYPE: DNA
<213> ORGANISM: Homo sapiens
<220> FEATURE:
<221> NAME/KEY: CDS
<222> LOCATION: (7)..(1860)
<300> PUBLICATION INFORMATION:
<302> TITLE: Molecular cloning and functional characterization of a
      novel mammalian sphingosine kinase type 2 isoform
<303> JOURNAL: J. Biol. Chem.
<304> VOLUME: 275
<305> ISSUE: 26
<306> PAGES: 19513-19520
<307> DATE: 2000-06-30
<308> DATABASE ACCESSION NUMBER: AF245447
<309> DATABASE ENTRY DATE: 2000-06-27

<400> SEQUENCE: 13

```
gccacc atg gcc ccg ccc cca ccg cca ctg gct gcc agc acc ccg ctc      48
       Met Ala Pro Pro Pro Pro Pro Leu Ala Ala Ser Thr Pro Leu
        1               5                  10 ctc cat ggc gag ttt ggc tcc tac cca gcc cga ggc cca cgc ttt gcc    96
Leu His Gly Glu Phe Gly Ser Tyr Pro Ala Arg Gly Pro Arg Phe Ala
 15                  20                  25                  30 ctc acc ctt aca tcg cag gcc ctg cac ata cag cgg ctg cgc ccc aaa   144
Leu Thr Leu Thr Ser Gln Ala Leu His Ile Gln Arg Leu Arg Pro Lys
                 35                  40                  45 cct gaa gcc agg ccc cgg ggt ggc ctg gtc ccg ttg gcc gag gtc tca   192
Pro Glu Ala Arg Pro Arg Gly Gly Leu Val Pro Leu Ala Glu Val Ser
             50                  55                  60
```

```
ggc tgc tgc acc ctg cga agc cgc agc ccc tca gac tca gcg gcc tac      240
Gly Cys Cys Thr Leu Arg Ser Arg Ser Pro Ser Asp Ser Ala Ala Tyr
            65                  70                  75 ttc tgc atc tac acc tac cct cgg ggc cgg cgc ggg gcc cgg cgc aga      288
Phe Cys Ile Tyr Thr Tyr Pro Arg Gly Arg Arg Gly Ala Arg Arg Arg
        80                  85                  90 gcc act cgc acc ttc cgg gca gat ggg gcc gcc acc tac gaa gag aac      336
Ala Thr Arg Thr Phe Arg Ala Asp Gly Ala Ala Thr Tyr Glu Glu Asn
95                  100                 105                 110 cgt gcc gag gcc cag cgc tgg gcc act gcc ctc acc tgt ctg ctc cga      384
Arg Ala Glu Ala Gln Arg Trp Ala Thr Ala Leu Thr Cys Leu Leu Arg
                115                 120                 125 gga ctg cca ctg ccc ggg gat ggg gag atc acc cct gac ctg cta cct      432
Gly Leu Pro Leu Pro Gly Asp Gly Glu Ile Thr Pro Asp Leu Leu Pro
            130                 135                 140 cgg ccg ccc cgg ttg ctt cta ttg gtc aat ccc ttt ggg ggt cgg ggc      480
Arg Pro Pro Arg Leu Leu Leu Leu Val Asn Pro Phe Gly Gly Arg Gly
        145                 150                 155 ctg gcc tgg cag tgg tgt aag aac cac gtg ctt ccc atg atc tct gaa      528
Leu Ala Trp Gln Trp Cys Lys Asn His Val Leu Pro Met Ile Ser Glu
160                 165                 170 gct ggg ctg tcc ttc aac ctc atc cag aca gaa cga cag aac cac gcc      576
Ala Gly Leu Ser Phe Asn Leu Ile Gln Thr Glu Arg Gln Asn His Ala
175                 180                 185                 190 cgg gag ctg gtc cag ggg ctg agc ctg agt gag tgg gat ggc atc gtc      624
Arg Glu Leu Val Gln Gly Leu Ser Leu Ser Glu Trp Asp Gly Ile Val
                195                 200                 205 acg gtc tcg gga gac ggg ctg ctc cat gag gtg ctg aac ggg ctc cta      672
Thr Val Ser Gly Asp Gly Leu Leu His Glu Val Leu Asn Gly Leu Leu
            210                 215                 220 gat cgc cct gac tgg gag gaa gct gtg aag atg cct gtg ggc atc ctc      720
Asp Arg Pro Asp Trp Glu Glu Ala Val Lys Met Pro Val Gly Ile Leu
        225                 230                 235 ccc tgc ggc tcg ggc aac gcg ctg gcc gga gca gtg aac cag cac ggg      768
Pro Cys Gly Ser Gly Asn Ala Leu Ala Gly Ala Val Asn Gln His Gly
240                 245                 250 gga ttt gag cca gcc ctg ggc ctc gac ctg ttg ctc aac tgc tca ctg      816
Gly Phe Glu Pro Ala Leu Gly Leu Asp Leu Leu Leu Asn Cys Ser Leu
255                 260                 265                 270 ttg ctg tgc cgg ggt ggt ggc cac cca ctg gac ctg ctc tcc gtg acg      864
Leu Leu Cys Arg Gly Gly Gly His Pro Leu Asp Leu Leu Ser Val Thr
                275                 280                 285 ctg gcc tcg ggc tcc cgc tgt ttc tcc ttc ctg tct gtg gcc tgg ggc      912
Leu Ala Ser Gly Ser Arg Cys Phe Ser Phe Leu Ser Val Ala Trp Gly
            290                 295                 300 ttc gtg tca gat gtg gat atc cag agc gag cgc ttc agg gcc ttg ggc      960
Phe Val Ser Asp Val Asp Ile Gln Ser Glu Arg Phe Arg Ala Leu Gly
        305                 310                 315 agt gcc cgc ttc aca ctg ggc acg gtg ctg ggc ctc gcc aca ctg cac     1008
Ser Ala Arg Phe Thr Leu Gly Thr Val Leu Gly Leu Ala Thr Leu His
320                 325                 330 acc tac cgc gga cgc ctc tcc tac ctc ccc gcc act gtg gaa cct gcc     1056
Thr Tyr Arg Gly Arg Leu Ser Tyr Leu Pro Ala Thr Val Glu Pro Ala
335                 340                 345                 350 tcg ccc acc cct gcc cat agc ctg cct cgt gcc aag tcg gag ctg acc     1104
Ser Pro Thr Pro Ala His Ser Leu Pro Arg Ala Lys Ser Glu Leu Thr
                355                 360                 365 cta acc cca gac cca gcc ccg ccc atg gcc cac tca ccc ctg cat cgt     1152
Leu Thr Pro Asp Pro Ala Pro Pro Met Ala His Ser Pro Leu His Arg
```

-continued

```
                     370                 375                 380
tct gtg tct gac ctg cct ctt ccc ctg ccc cag cct gcc ctg gcc tct    1200
Ser Val Ser Asp Leu Pro Leu Pro Leu Pro Gln Pro Ala Leu Ala Ser
            385                 390                 395 cct ggc tcg cca gaa ccc ctg ccc atc ctg tcc ctc aac ggt ggg ggc    1248
Pro Gly Ser Pro Glu Pro Leu Pro Ile Leu Ser Leu Asn Gly Gly Gly
        400                 405                 410 cca gag ctg gct ggg gac tgg ggt ggg gct ggg gat gct ccg ctg tcc    1296
Pro Glu Leu Ala Gly Asp Trp Gly Gly Ala Gly Asp Ala Pro Leu Ser
415                 420                 425                 430 ccg gac cca ctg ctg tct tca cct cct ggc tct ccc aag gca gct cta    1344
Pro Asp Pro Leu Leu Ser Ser Pro Pro Gly Ser Pro Lys Ala Ala Leu
                435                 440                 445 cac tca ccc gtc tcc gaa ggg gcc ccc gta att ccc cca tcc tct ggg    1392
His Ser Pro Val Ser Glu Gly Ala Pro Val Ile Pro Pro Ser Ser Gly
            450                 455                 460 ctc cca ctt ccc acc cct gat gcc cgg gta ggg gcc tcc acc tgc ggc    1440
Leu Pro Leu Pro Thr Pro Asp Ala Arg Val Gly Ala Ser Thr Cys Gly
        465                 470                 475 ccg ccc gac cac ctg ctg cct ccg ctg ggc acc ccg ctg ccc cca gac    1488
Pro Pro Asp His Leu Leu Pro Pro Leu Gly Thr Pro Leu Pro Pro Asp
480                 485                 490 tgg gtg acg ctg gag ggg gac ttt gtg ctc atg ttg gcc atc tcg ccc    1536
Trp Val Thr Leu Glu Gly Asp Phe Val Leu Met Leu Ala Ile Ser Pro
495                 500                 505                 510 agc cac cta ggc gct gac ctg gtg gca gct ccg cat gcg cgc ttc gac    1584
Ser His Leu Gly Ala Asp Leu Val Ala Ala Pro His Ala Arg Phe Asp
                515                 520                 525 gac ggc ctg gtg cac ctg tgc tgg gtg cgt agc ggc atc tcg cgg gct    1632
Asp Gly Leu Val His Leu Cys Trp Val Arg Ser Gly Ile Ser Arg Ala
            530                 535                 540 gcg ctg ctg cgc ctt ttc ttg gcc atg gag cgt ggt agc cac ttc agc    1680
Ala Leu Leu Arg Leu Phe Leu Ala Met Glu Arg Gly Ser His Phe Ser
        545                 550                 555 ctg ggc tgt ccg cag ctg ggc tac gcc gcg gcc cgt gcc ttc cgc cta    1728
Leu Gly Cys Pro Gln Leu Gly Tyr Ala Ala Ala Arg Ala Phe Arg Leu
560                 565                 570 gag ccg ctc aca cca cgc ggc gtg ctc aca gtg gac ggg gag cag gtg    1776
Glu Pro Leu Thr Pro Arg Gly Val Leu Thr Val Asp Gly Glu Gln Val
575                 580                 585                 590 gag tat ggg ccg cta cag gca cag atg cac cct ggc atc ggt aca ctg    1824
Glu Tyr Gly Pro Leu Gln Ala Gln Met His Pro Gly Ile Gly Thr Leu
                595                 600                 605 ctc act ggg cct cct ggc tgc ccg ggg cgg gag ccc tgaaactaaa         1870
Leu Thr Gly Pro Pro Gly Cys Pro Gly Arg Glu Pro
            610                 615 caagcttggt acccgccggg ggcggggcct acattccaat ggggcggagc ttgagctagg  1930
gggtgtggcc tggctgctag agttgtggtg cagggggccc tggccccgtc tcaggattgc  1990
gctcgctttc atgggaccag acgtgatgct ggaaggtggg cgtcgtcacg gttaaagaga  2050
aatgggctcg tcccgagggt agtgcctgat caatgagggc ggggcctggc gtctgatctg  2110
gggccgccct tacggggcag ggctcagtcc tgacgcttgc cacctgctcc tacccggcca  2170
ggatggctga gggcggagtc tattttacgc gtcgcccaat gacaggacct ggaatgtact  2230 ggctgggta ggcctcagtg agtcggccgg tcagggcccg cagcctcgcc ccatccactc   2290
cggtgcctcc atttagctgg ccaatcagcc caggaggggc aggttccccg gggccggcgc  2350
taggatttgc actaatgttc ctctccccgc                                   2380
```

<210> SEQ ID NO 14
<211> LENGTH: 618
<212> TYPE: PRT
<213> ORGANISM: Homo sapiens

<400> SEQUENCE: 14

Met Ala Pro Pro Pro Pro Leu Ala Ala Ser Thr Pro Leu Leu His
1               5                   10                  15

Gly Glu Phe Gly Ser Tyr Pro Ala Arg Gly Pro Arg Phe Ala Leu Thr
            20                  25                  30

Leu Thr Ser Gln Ala Leu His Ile Gln Arg Leu Arg Pro Lys Pro Glu
        35                  40                  45

Ala Arg Pro Arg Gly Gly Leu Val Pro Leu Ala Glu Val Ser Gly Cys
    50                  55                  60

Cys Thr Leu Arg Ser Arg Ser Pro Ser Asp Ser Ala Ala Tyr Phe Cys
65                  70                  75                  80

Ile Tyr Thr Tyr Pro Arg Gly Arg Arg Gly Ala Arg Arg Ala Thr
                85                  90                  95

Arg Thr Phe Arg Ala Asp Gly Ala Ala Thr Tyr Glu Glu Asn Arg Ala
                100                 105                 110

Glu Ala Gln Arg Trp Ala Thr Ala Leu Thr Cys Leu Leu Arg Gly Leu
            115                 120                 125

Pro Leu Pro Gly Asp Gly Glu Ile Thr Pro Asp Leu Leu Pro Arg Pro
        130                 135                 140

Pro Arg Leu Leu Leu Leu Val Asn Pro Phe Gly Gly Arg Gly Leu Ala
145                 150                 155                 160

Trp Gln Trp Cys Lys Asn His Val Leu Pro Met Ile Ser Glu Ala Gly
                165                 170                 175

Leu Ser Phe Asn Leu Ile Gln Thr Glu Arg Gln Asn His Ala Arg Glu
            180                 185                 190

Leu Val Gln Gly Leu Ser Leu Ser Glu Trp Asp Gly Ile Val Thr Val
        195                 200                 205

Ser Gly Asp Gly Leu Leu His Glu Val Leu Asn Gly Leu Leu Asp Arg
    210                 215                 220

Pro Asp Trp Glu Glu Ala Val Lys Met Pro Val Gly Ile Leu Pro Cys
225                 230                 235                 240

Gly Ser Gly Asn Ala Leu Ala Gly Ala Val Asn Gln His Gly Gly Phe
                245                 250                 255

Glu Pro Ala Leu Gly Leu Asp Leu Leu Leu Asn Cys Ser Leu Leu Leu
            260                 265                 270

Cys Arg Gly Gly His Pro Leu Asp Leu Leu Ser Val Thr Leu Ala
        275                 280                 285

Ser Gly Ser Arg Cys Phe Ser Phe Leu Ser Val Ala Trp Gly Phe Val
    290                 295                 300

Ser Asp Val Asp Ile Gln Ser Glu Arg Phe Arg Ala Leu Gly Ser Ala
305                 310                 315                 320

Arg Phe Thr Leu Gly Thr Val Leu Gly Leu Ala Thr Leu His Thr Tyr
                325                 330                 335

Arg Gly Arg Leu Ser Tyr Leu Pro Ala Thr Val Glu Pro Ala Ser Pro
            340                 345                 350

Thr Pro Ala His Ser Leu Pro Arg Ala Lys Ser Glu Leu Thr Leu Thr
        355                 360                 365

Pro Asp Pro Ala Pro Pro Met Ala His Ser Pro Leu His Arg Ser Val

-continued

```
                    370                 375                 380
Ser Asp Leu Pro Leu Pro Leu Pro Gln Pro Ala Leu Ala Ser Pro Gly
385                 390                 395                 400

Ser Pro Glu Pro Leu Pro Ile Leu Ser Leu Asn Gly Gly Gly Pro Glu
                405                 410                 415

Leu Ala Gly Asp Trp Gly Gly Ala Gly Asp Ala Pro Leu Ser Pro Asp
            420                 425                 430

Pro Leu Leu Ser Ser Pro Pro Gly Ser Pro Lys Ala Ala Leu His Ser
                435                 440                 445

Pro Val Ser Glu Gly Ala Pro Val Ile Pro Pro Ser Ser Gly Leu Pro
450                 455                 460

Leu Pro Thr Pro Asp Ala Arg Val Gly Ala Ser Thr Cys Gly Pro Pro
465                 470                 475                 480

Asp His Leu Leu Pro Pro Leu Gly Thr Pro Leu Pro Pro Asp Trp Val
                485                 490                 495

Thr Leu Glu Gly Asp Phe Val Leu Met Leu Ala Ile Ser Pro Ser His
                500                 505                 510

Leu Gly Ala Asp Leu Val Ala Ala Pro His Ala Arg Phe Asp Asp Gly
            515                 520                 525

Leu Val His Leu Cys Trp Val Arg Ser Gly Ile Ser Arg Ala Ala Leu
530                 535                 540

Leu Arg Leu Phe Leu Ala Met Glu Arg Gly Ser His Phe Ser Leu Gly
545                 550                 555                 560

Cys Pro Gln Leu Gly Tyr Ala Ala Ala Arg Ala Phe Arg Leu Glu Pro
                565                 570                 575

Leu Thr Pro Arg Gly Val Leu Thr Val Asp Gly Glu Gln Val Glu Tyr
            580                 585                 590

Gly Pro Leu Gln Ala Gln Met His Pro Gly Ile Gly Thr Leu Leu Thr
                595                 600                 605

Gly Pro Pro Gly Cys Pro Gly Arg Glu Pro
            610                 615
```

<210> SEQ ID NO 15
<211> LENGTH: 388
<212> TYPE: PRT
<213> ORGANISM: Mus musculus
<300> PUBLICATION INFORMATION:
<302> TITLE: Molecular cloning and functional characterization of
    murine sphingosine kinase
<303> JOURNAL: J. Biol. Chem.
<304> VOLUME: 273
<305> ISSUE: 37
<306> PAGES: 23722-23728
<307> DATE: 1998-09-11
<308> DATABASE ACCESSION NUMBER: AAC61698
<309> DATABASE ENTRY DATE: 1998-09-26

<400> SEQUENCE: 15

```
Met Trp Trp Cys Cys Val Leu Phe Val Val Glu Cys Pro Arg Gly Leu
1               5                   10                  15

Leu Pro Arg Pro Cys Arg Val Leu Val Leu Asn Pro Gln Gly Gly
                20                  25                  30

Lys Gly Lys Ala Leu Gln Leu Phe Gln Ser Arg Val Gln Pro Phe Leu
            35                  40                  45

Glu Glu Ala Glu Ile Thr Phe Lys Leu Ile Leu Thr Glu Arg Lys Asn
        50                  55                  60

His Ala Arg Glu Leu Val Cys Ala Glu Glu Leu Gly His Trp Asp Ala
65                  70                  75                  80
```

-continued

```
Leu Ala Val Met Ser Gly Asp Gly Leu Met His Glu Val Val Asn Gly
            85                  90                  95

Leu Met Glu Arg Pro Asp Trp Glu Thr Ala Ile Gln Lys Pro Leu Cys
           100                 105                 110

Ser Leu Pro Gly Gly Ser Gly Asn Ala Leu Ala Ala Ser Val Asn His
           115                 120                 125

Tyr Ala Gly Tyr Glu Gln Val Thr Asn Glu Asp Leu Leu Ile Asn Cys
           130                 135                 140

Thr Leu Leu Leu Cys Arg Arg Arg Leu Ser Pro Met Asn Leu Leu Ser
145                 150                 155                 160

Leu His Thr Ala Ser Gly Leu Arg Leu Tyr Ser Val Leu Ser Leu Ser
               165                 170                 175

Trp Gly Phe Val Ala Asp Val Asp Leu Glu Ser Glu Lys Tyr Arg Arg
               180                 185                 190

Leu Gly Glu Ile Arg Phe Thr Val Gly Thr Phe Phe Arg Leu Ala Ser
           195                 200                 205

Leu Arg Ile Tyr Gln Gly Gln Leu Ala Tyr Leu Pro Val Gly Thr Val
           210                 215                 220

Ala Ser Lys Arg Pro Ala Ser Thr Leu Val Gln Lys Gly Pro Val Asp
225                 230                 235                 240

Thr His Leu Val Pro Leu Glu Glu Pro Val Pro Ser His Trp Thr Val
               245                 250                 255

Val Pro Glu Gln Asp Phe Val Leu Val Leu Val Leu Leu His Thr His
           260                 265                 270

Leu Ser Ser Glu Leu Phe Ala Ala Pro Met Gly Arg Cys Glu Ala Gly
           275                 280                 285

Val Met His Leu Phe Tyr Val Arg Ala Gly Val Ser Arg Ala Ala Leu
           290                 295                 300

Leu Arg Leu Phe Leu Ala Met Gln Lys Gly Lys His Met Glu Leu Asp
305                 310                 315                 320

Cys Pro Tyr Leu Val His Val Pro Val Val Ala Phe Arg Leu Glu Pro
               325                 330                 335

Arg Ser Gln Arg Gly Val Phe Ser Val Asp Gly Glu Leu Met Val Cys
               340                 345                 350

Glu Ala Val Gln Gly Gln Val His Pro Asn Tyr Leu Trp Met Val Cys
           355                 360                 365

Gly Ser Arg Asp Ala Pro Ser Gly Arg Asp Ser Arg Arg Gly Pro Pro
           370                 375                 380

Pro Glu Glu Pro
385
```